United States Patent
Boock et al.

(10) Patent No.: US 12,161,466 B2
(45) Date of Patent: *Dec. 10, 2024

(54) WORKING ELECTRODE OF A CONTINUOUS BIOLOGICAL SENSOR

(71) Applicant: Allez Health Inc., Carlsbad, CA (US)

(72) Inventors: Robert James Boock, Carlsbad, CA (US); Huashi Zhang, San Juan Capistrano, CA (US)

(73) Assignee: Allez Health Inc., Carlsbad, CA (US)

(*) Notice: Subject to any disclaimer, the term of this patent is extended or adjusted under 35 U.S.C. 154(b) by 352 days.

This patent is subject to a terminal disclaimer.

(21) Appl. No.: 17/446,735

(22) Filed: Sep. 2, 2021

(65) Prior Publication Data

US 2021/0393179 A1 Dec. 23, 2021

Related U.S. Application Data

(62) Division of application No. 16/375,884, filed on Apr. 5, 2019, now Pat. No. 11,134,874.

(Continued)

(51) Int. Cl.
*A61B 5/1486* (2006.01)
*A61B 5/145* (2006.01)
(Continued)

(52) U.S. Cl.
CPC ...... *A61B 5/14865* (2013.01); *A61B 5/14532* (2013.01); *C12N 9/0006* (2013.01);
(Continued)

(58) Field of Classification Search
CPC ... A61B 5/14865; A61B 5/1473; A61B 5/145; C12Q 1/00; C12Q 1/006; G01N 33/487; G01N 27/26; C12N 9/006
See application file for complete search history.

(56) References Cited

U.S. PATENT DOCUMENTS

| | | |
|---|---|---|
| 4,440,175 A | 4/1984 | Wilkins |
| 6,905,733 B2 | 6/2005 | Russell et al. |

(Continued)

FOREIGN PATENT DOCUMENTS

| | | |
|---|---|---|
| CN | 110702764 A | 1/2020 |
| EP | 0649628 A1 | 4/1995 |

(Continued)

OTHER PUBLICATIONS

Basu A, Veettil S, Dyer R, Peyser T, Basu R. "Direct Evidence of Acetaminophen Interference with Subcutaneous Glucose Sensing in Humans: A Pilot Study." Diabetes Technol Ther. Feb. 2016;18 Suppl 2(Suppl 2):S243-7. doi: 10.1089/dia.2015.0410. PMID: 26784129; PMCID: PMC4717519. (Year: 2016).

(Continued)

*Primary Examiner* — Dah-Wei D. Yuan
*Assistant Examiner* — Andrew J Bowman
(74) *Attorney, Agent, or Firm* — MLO, a professional corp.

(57) ABSTRACT

A working electrode for a subcutaneous sensor for use with a continuous biological monitor for a patient is disclosed. The working electrode includes a conductive substrate and a carbon-enzyme layer on the conductive substrate. The carbon-enzyme layer includes a polyurethane or silicone crosslinked with an acrylic polyol, and an enzyme fully entrapped by the polyurethane or silicone crosslinked with the acrylic polyol. The enzyme is selected according to a biological function to be monitored. The carbon-enzyme layer also includes a carbon material. The carbon-enzyme layer is electrically conductive and facilitates a generation of either peroxide or electrons within the carbon-enzyme layer responsive to reacting the enzyme with a target biologic from blood of the patient.

20 Claims, 19 Drawing Sheets

Related U.S. Application Data

(60) Provisional application No. 62/796,832, filed on Jan. 25, 2019, provisional application No. 62/796,842, filed on Jan. 25, 2019, provisional application No. 62/653,821, filed on Apr. 6, 2018.

(51) Int. Cl.

| | |
|---|---|
| *C12N 9/04* | (2006.01) |
| *C12Q 1/00* | (2006.01) |
| *C25D 7/06* | (2006.01) |
| *C25D 9/02* | (2006.01) |
| *G01N 27/327* | (2006.01) |
| *H01M 4/02* | (2006.01) |
| *H01M 4/04* | (2006.01) |
| *H01M 4/1395* | (2010.01) |
| *H01M 4/1399* | (2010.01) |
| *H01M 4/96* | (2006.01) |

(52) U.S. Cl.
CPC ............ *C12Q 1/002* (2013.01); *C12Q 1/006* (2013.01); *C25D 7/0607* (2013.01); *C25D 9/02* (2013.01); *G01N 27/3271* (2013.01); *G01N 27/3275* (2013.01); *H01M 4/02* (2013.01); *H01M 4/0402* (2013.01); *H01M 4/0419* (2013.01); *H01M 4/045* (2013.01); *H01M 4/1395* (2013.01); *H01M 4/1399* (2013.01); *H01M 4/96* (2013.01); *A61B 2562/125* (2013.01); *C12Y 101/01027* (2013.01); *C12Y 101/0103* (2013.01); *C12Y 101/03004* (2013.01); *H01M 2004/024* (2013.01)

(56) References Cited

U.S. PATENT DOCUMENTS

| | | | |
|---|---|---|---|
| 7,828,728 B2 | 11/2010 | Boock et al. | |
| 7,951,869 B2 | 5/2011 | Funston | |
| 8,414,750 B2 | 4/2013 | Heller et al. | |
| 8,420,740 B2 | 4/2013 | Smith et al. | |
| 8,900,431 B2 | 12/2014 | Curry et al. | |
| 8,906,210 B2 | 12/2014 | Curry | |
| 11,134,874 B2 * | 10/2021 | Boock ................ | A61B 5/14532 |
| 2003/0129314 A1 | 7/2003 | Russell et al. | |
| 2003/0217966 A1 | 11/2003 | Tapsak et al. | |
| 2004/0073295 A1 | 4/2004 | Chaikof et al. | |
| 2004/0106166 A1 | 6/2004 | Matsumoto | |
| 2006/0289307 A1 | 12/2006 | Yu et al. | |
| 2007/0027458 A1 | 2/2007 | Brister et al. | |
| 2007/0173711 A1 | 7/2007 | Shah et al. | |
| 2007/0197889 A1 | 8/2007 | Brister et al. | |
| 2007/0197890 A1 | 8/2007 | Boock et al. | |
| 2008/0279909 A1 | 11/2008 | Cleek et al. | |
| 2009/0062767 A1 | 3/2009 | Antwerp et al. | |
| 2009/0101498 A1 | 4/2009 | Papadimitrakopoulos et al. | |
| 2009/0203978 A1 | 8/2009 | Say et al. | |
| 2009/0247856 A1 | 10/2009 | Boock et al. | |
| 2010/0025238 A1 | 2/2010 | Gottlieb et al. | |
| 2010/0270175 A1 | 10/2010 | Pei et al. | |
| 2010/0286786 A1 | 11/2010 | Kita et al. | |
| 2011/0027458 A1 | 2/2011 | Boock et al. | |
| 2011/0028815 A1 | 2/2011 | Simpson et al. | |
| 2011/0144465 A1 | 6/2011 | Shults et al. | |
| 2011/0230735 A1 | 9/2011 | Wolfe et al. | |
| 2012/0067734 A1 | 3/2012 | Wang et al. | |
| 2013/0053666 A1 | 2/2013 | Hughes et al. | |
| 2013/0189720 A1 | 7/2013 | Petisce | |
| 2014/0262831 A1 | 9/2014 | Balasubramanian et al. | |
| 2014/0305804 A1 | 10/2014 | Madangopal et al. | |
| 2014/0348703 A1 | 11/2014 | Thomas et al. | |
| 2014/0367246 A1 | 12/2014 | Shah et al. | |
| 2014/0371695 A1 | 12/2014 | Chiang et al. | |
| 2015/0025346 A1 | 1/2015 | Simpson et al. | |
| 2015/0038815 A1 | 2/2015 | Boock et al. | |
| 2015/0122645 A1 | 5/2015 | Yang et al. | |
| 2015/0122647 A1 | 5/2015 | Shah et al. | |
| 2015/0366493 A1 | 12/2015 | Cremers | |
| 2017/0156652 A1 | 6/2017 | Qiang et al. | |
| 2017/0164881 A1 | 6/2017 | Fujita et al. | |
| 2017/0188916 A1 * | 7/2017 | Wang ..................... | C12Q 1/006 |
| 2017/0188921 A1 | 7/2017 | Wang et al. | |
| 2017/0191955 A1 | 7/2017 | Zou et al. | |
| 2017/0258378 A1 | 9/2017 | Eshoo et al. | |
| 2017/0290512 A1 | 10/2017 | Antonio et al. | |
| 2017/0325723 A1 | 11/2017 | Larson et al. | |
| 2017/0347933 A1 | 12/2017 | Wang | |
| 2018/0094290 A1 | 4/2018 | Feldman et al. | |
| 2019/0142317 A1 | 5/2019 | Steedman et al. | |
| 2019/0310218 A1 | 10/2019 | Boock et al. | |
| 2019/0310219 A1 | 10/2019 | Boock | |
| 2019/0320947 A1 | 10/2019 | Chen et al. | |
| 2020/0085341 A1 | 3/2020 | Windmiller | |
| 2020/0196924 A1 | 6/2020 | Brister | |
| 2021/0393179 A1 | 12/2021 | Boock et al. | |

FOREIGN PATENT DOCUMENTS

| | | |
|---|---|---|
| EP | 2017607 B1 | 10/2012 |
| EP | 2759411 A1 | 7/2014 |
| WO | 2016049243 A1 | 3/2016 |
| WO | 2018107168 A1 | 6/2018 |
| WO | 2021250527 A1 | 12/2021 |
| WO | 2022149015 A1 | 7/2022 |

OTHER PUBLICATIONS

European Search Report dated Apr. 5, 2023 for European Patent Office Patent Application No. 23158880.7.
Inoglu N et al: "Glucose oxidase immobilization by polyurethane film/foam in dense CO2 environment", Process Biochemistry, Elsevier Ltd, GB, vol. 43, No. 3, Mar. 1, 2008 (Mar. 1, 2008), pp. 271-279, [retrieved on Dec. 27, 2007].
Kilinc et al. "Comparison of electrochemical detection of acetylcholine-induced nitric oxide release (NO) and contractile force measurement of rabbit isolated carotid artery endothelium", Journal of Pharmaceutical and Biomedical Analysis, 2002, vol. 28, pp. 345-354. (Year: 2002). Turkey.
Office Action dated Apr. 3, 2023 for U.S. Appl. No. 17/449,380.
Office Action dated Mar. 7, 2023 for U.S. Appl. No. 16/375,875.
Sarah J. Killoran, Robert D. O'Neill, "Characterization of permselective coatings electrosynthesized on Pt—Ir from the three phenylenediamine isomers for biosensor applications," Electrochimica Acta, col. 3, issue 24, pp. 7303-7312 (Year: 2008).
Zhang et al. "pH manipulation: A Facile Method for Lowering Oxidation State and Keeping Good Yield of Poly(m-phenylenediamine) and Its Powerful Ag+ Adsorption Ability", Langumuir, 2011, vol. 27, pp. 13729-13738. (Year: 2011). China.
Notice of Allowance and Fees dated Oct. 19, 2022 for U.S. Appl. No. 16/375,873.
Notice of Allowance and Fees dated Oct. 20, 2021 for U.S. Appl. No. 16/375,887.
Abdullahi Mohamed Farah et al., "Electrochemical Detection of Hydrogen Peroxide Based on Graphene Oxide/Prussian Blue Modified Glassy Carbon Electrode," Int. J. Electrochem. Sci., 7 (Jun. 2012) 5069-5083.
Audrey L. Sanford et al., "Voltammetric Detection of Hydrogen Peroxide at Carbon Fiber Microelectrodes", Anal. Chem., Jun. 15, 2010; 82(12): 5205-5210. doi: 10.1021/ac100536s.
Chris Phillips et al., "The effect of graphite and carbon black ratios on conductive ink performance," J Mater Sci (Apr. 2017), 52:9520-9530.
International Search Report dated Jul. 30, 2019 for PCT Patent Application No. PCT/US2019/025962.
International Search Report dated Oct. 29, 2019 for PCT Patent Application No. PCT/US2019/026028.
Notice of Allowance and Fees dated Jun. 8, 2021 for U.S. Appl. No. 16/375,884.

(56) References Cited

OTHER PUBLICATIONS

Notice of Allowance dated Apr. 14, 2021 for U.S. Appl. No. 16/375,880.
Office Action dated Apr. 27, 2021 for U.S. Appl. No. 16/375,887.
Office Action dated Feb. 8, 2021 for U.S. Appl. No. 16/375,884.
Office Action dated Jan. 21, 2021 for U.S. Appl. No. 16/375,887.
Paul James Brigandi, "Electrically Conductive Multiphase Polymer Blend Carbon-Based Composites," Theses, Leigh University, 2014, Paper 1438.
Qian Wang, "Carbon-based Materials: Application in Electrochemical Sensing," Thesis, Universite de Lille, France, Oct. 2016.
Restriction Requirement dated Dec. 30, 2020 for U.S. Appl. No. 16/375,880.
Ricardo Tucceri, "Non-Conducting Poly(O-Aminophenol) Films in the Field of the Bioelectrochemistry," American Journal of Analytical Chemistry, 2013, 4, 13-26, http://dx.doi.org/10.4236/ajac.2013.46A003 Published Online Jun. 2013 (http://www.scirp.org/journal/ajac).
Ricardo Tucceri, et al., "Electrosynthesis and Spectroscopic Characterization of Poly(o-Aminophenol) Film Electrodes," International Scholarly Research Network, ISRN Polymer Science, May 2012, vol. 2012, Article ID 942920, 26 pages, doi:10.5402/2012/942920.
Screen-Printed Carbon Electrodes, DropSens, 2 pages, Accessed on Mar. 15, 2018.
Shin, J. et al., Potentiometric biosensors using immobilized enzyme layers mixed with hydrophilic polyurethane, Sensors and Actuators B 50, Mar. 24, 1998, 8 pgs, Elsevier, Korea.
Notice of Allowance and Fees dated Aug. 3, 2022 for U.S. Appl. No. 16/375,891.
Notice of Allowance and Fees dated Aug. 3, 2022 for U.S. Appl. No. 16/375,895.
Office Action dated Aug. 4, 2022 for U.S. Appl. No. 16/375,875.
Office Action dated Oct. 5, 2022 for U.S. Appl. No. 16/375,877.
Spyropoulos et al., "Fabrication and Utilization of Bifunctional Protein/Polysaccharide Coprecipitates for the Independent Codelivery of Two Model Actives from Simple Oil-in-Water Emulsions", Langmuir, Mar. 2018, vol. 34, pp. 3934-3948 (Year: 2018).
Tucceri et al., "Electrosynthesis and Spectroscopic Characterization of Poly-o-Aminophenol) Film Electrodes", International Scholarly Research Notices, May 15, 2012, vol. 2012, Article ID 942920, 26 pages. (Year: 2012).
Office Action dated Apr. 12, 2022 for U.S. Appl. No. 16/375,891.
Office Action dated Apr. 14, 2022 for U.S. Appl. No. 16/375,877.
Office Action dated Apr. 7, 2022 for U.S. Appl. No. 16/375,895.
Office Action dated May 9, 2022 for U.S. Appl. No. 16/375,873.
European Search Report dated Jan. 28, 2022 for European Patent Application No. 19780733.2.
International Search Report and Written Opinion dated Mar. 8, 2022 for PCT Patent Application No. PCT/IB2021/061432.
Asano, A. (2017). Polymer Blends and Composites. In: Webb, G. (eds) Modern Magnetic Resonance. Springer, Cham. https://doi.org/10.1007/978-3-319-28275-6_57-1 (Year: 2017).
Mathias, Lon Jay. "Thoughts on Thermoplastic Elastomers," Polymer Science Learning Center, https://pslc.ws/macrog/level3.htm (Year: 2023).
Office Action dated Nov. 16, 2023 for U.S. Appl. No. 17/449,380.
Office Action dated Oct. 12, 2023 for U.S. Appl. No. 17/303,702.
Office Action dated Sep. 13, 2023 for U.S. Appl. No. 17/449,562.
Translation of (CN 110702764) (Year: 2023).
C. Saby et al: "Glucose sensor based on carbon paste electrode incorporating poly(ethylene glycol)-modified glucose oxidase and various mediators", Analytica Chimica Acta, vol. 304, No. 1, Mar. 1, 1995 (Mar. 1, 1995) pp. 33-39, XP055646277, Amsterdam, NL ISSN: 0003-2670, DOI:10.1016/0003-2670(94)00545-W.
Extended European Search Report dated Dec. 15, 2021 for European Patent Office Patent Application No. 19782061.6.
International Search Report and Written Opinion dated Jan. 3, 2022 for PCT Patent Application No. PCT/IB2021/058968.
International Search Report and Written Opinion dated Jan. 4, 2022 for PCT Patent Application No. PCT/IB2021/059023.
International Search Report and Written Opinion dated Oct. 21, 2021 for PCT Patent Application No. PCT/IB2021/054938.
Office Action dated Sep. 27, 2024 for U.S. Appl. No. 17/302,835.
Ionescu, 2005, "Chapter 10: Acrylic Polyols", in Chemistry and Technology of Polyols for Polyurethanes, iSmithers Rapra Publishing. Excerpt (3 pages total). Particularly Figure 10.1 and Reaction 10.1 . (Year: 2005).
European Search Report dated Sep. 17, 2024 for European Patent Office Patent Application No. 21877091.5.
European Search Report dated Sep. 19, 2024 for European Patent Office Patent Application No. 21877092.3.
Vardar Gokay et al.: "Synthesis of glucose oxidase-PEG aldehyde conjugates and improvement of enzymatic stability", Artificial Cells, Nanomedicine and Biotechnology, vol. 46, No. 4, May 19, 2018 (May 19, 2018), pp. 788-794, XP093201702, US ISSN: 2169-1401, DOI: 10.1080/21691401.2017.1345920.
Office Action dated May 8, 2024 for U.S. Appl. No. 17/303,702.
Office Action dated May 23, 2024 for U.S. Appl. No. 17/449,380.
Office Action dated May 10, 2024 for U.S. Appl. No. 17/449,562.
Dilbir Singh Bindra: "Development of potentially implantable glucose sensors. Item Type text; Dissertation—Reproduction (electronic) ", Dissertation, Jan. 1, 1990 (Jan. 1, 1990), XP093150956, the University of Arizona Retrieved from the Internet: URL:https://repository.arizona.edu/handle/10150/185235 [retrieved on Apr. 12, 2024].
European Search Report dated May 17, 2024 for European Patent Office Patent Application No. 21821827.9.
Office Action dated Jun. 5, 2024 for China Patent Application No. 201980024867.1.

\* cited by examiner

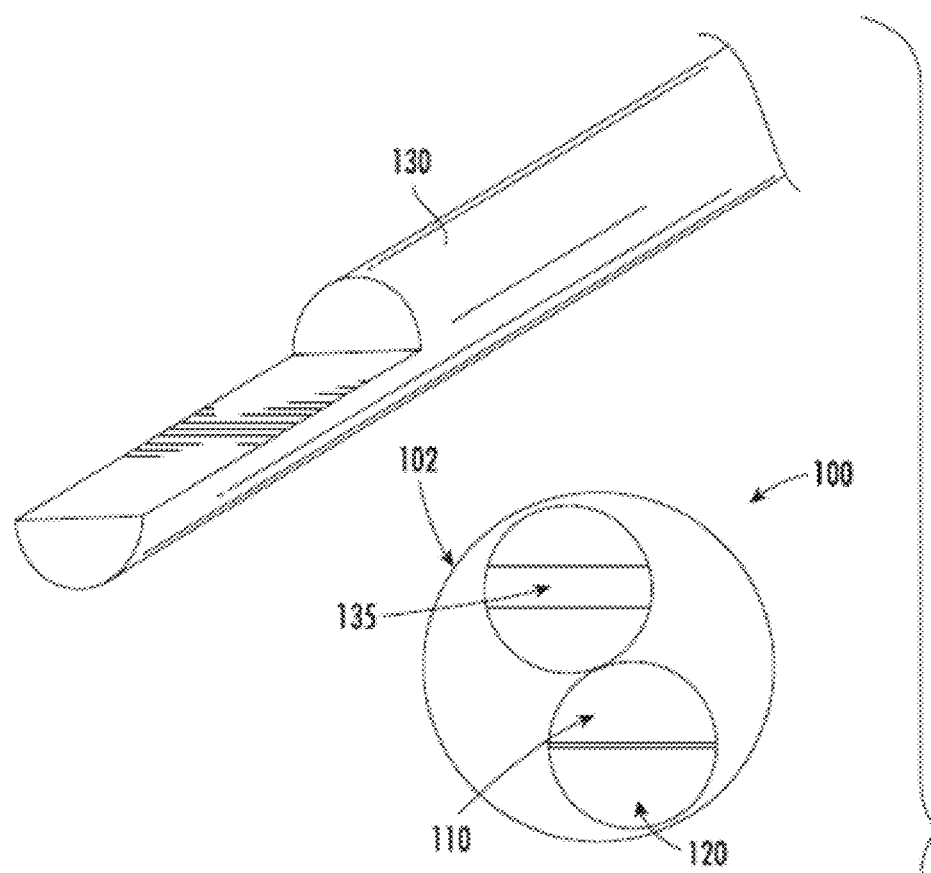
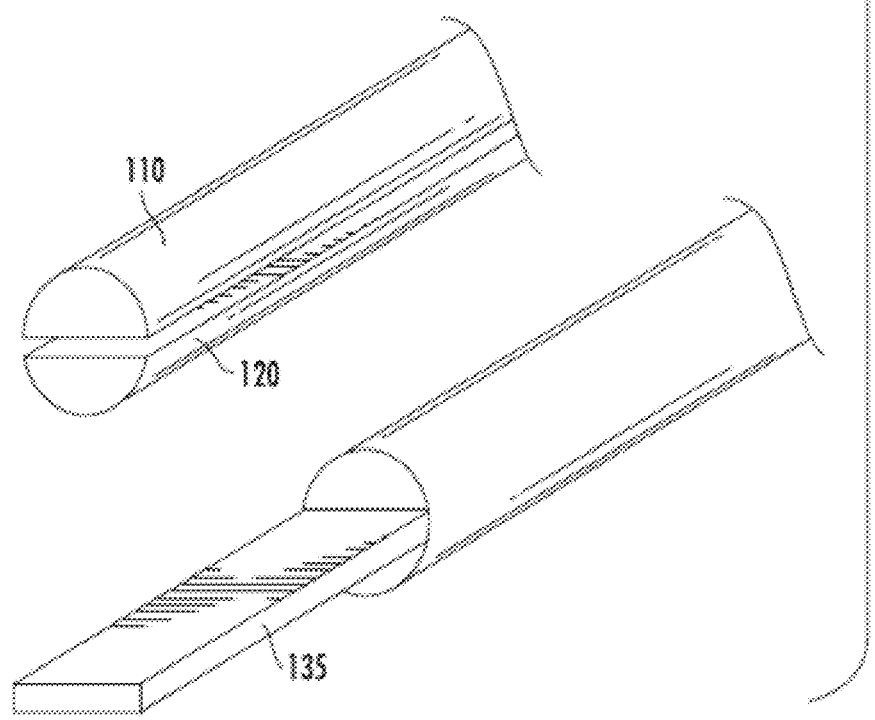
FIG. 1

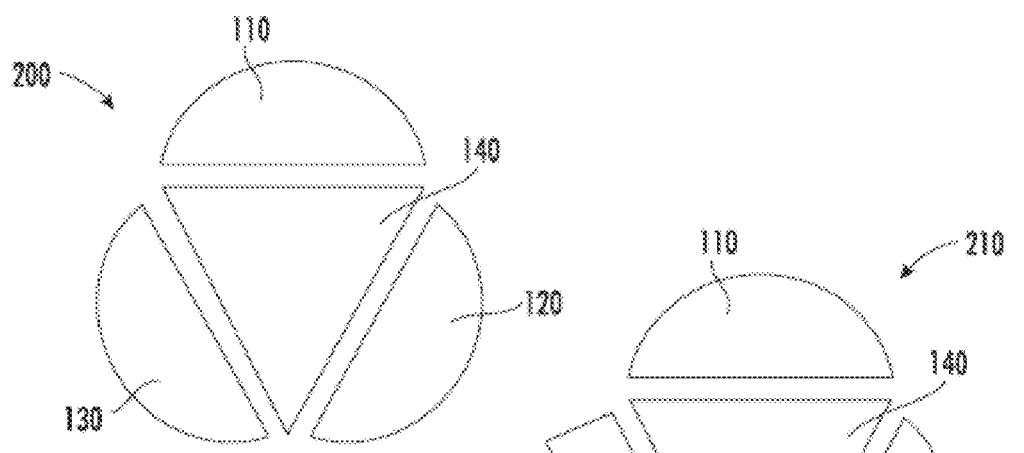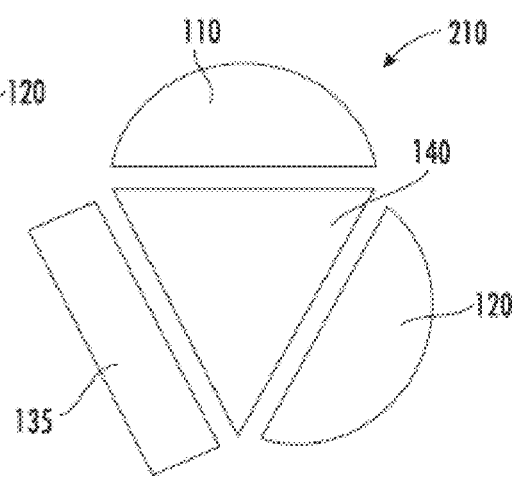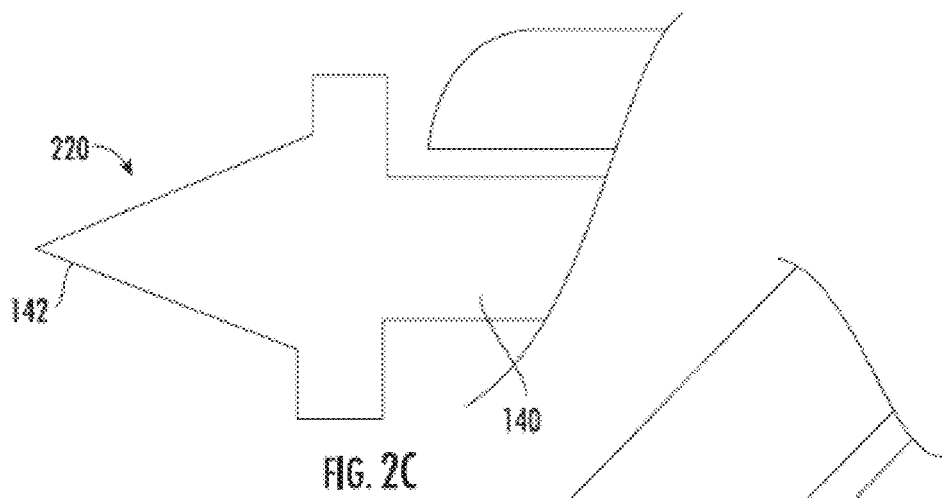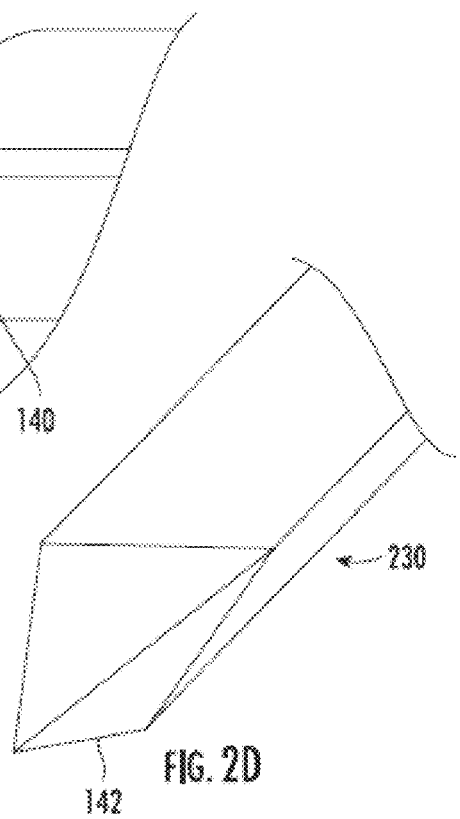

WORKING ELECTRODE OF A CONTINUOUS BIOLOGICAL SENSOR

RELATED APPLICATIONS

This application is a divisional of U.S. Non-Provisional patent application Ser. No. 16/375,884, filed Apr. 5, 2019, and entitled "Enhanced Carbon-Enzyme Membrane for a Working Electrode of a Continuous Biological Sensor"; which claims priority to (1) U.S. Provisional Application No. 62/653,821, filed Apr. 6, 2018, and entitled "Continuous Glucose Monitoring Device"; (2) U.S. Provisional Application No. 62/796,832, filed Jan. 25, 2019, and entitled "Carbon Working Electrode for a Continuous Biological Sensor"; and (3) U.S. Provisional Application No. 62/796,842, filed Jan. 25, 2019, and entitled "Enhanced Membrane Layers for the Working Electrode of a Continuous Biological Sensor"; each of which is incorporated herein by reference as if set forth in their entirety.

BACKGROUND

Monitoring of glucose levels is critical for diabetes patients. Continuous glucose monitoring (CGM) sensors are a type of device in which glucose is measured from fluid sampled in an area just under the skin multiple times a day. CGM devices typically involve a small housing in which the electronics are located and which is adhered to the patient's skin to be worn for a period of time. A small needle within the device delivers the subcutaneous sensor which is often electrochemical.

Glucose readings taken by the sensor can be tracked and analyzed by a monitoring device, such as by scanning the sensor with a customized receiver or by transmitting signals to a smartphone or other device that has an associated software application. Software features that have been included in CGM systems include viewing glucose levels over time, indicating glucose trends, and alerting the patient of high and low glucose levels.

Medical patients often have diseases or conditions that require the measurement and reporting of biological conditions. For example, if a patient has diabetes, it is important that the patient have an accurate understanding of the level of glucose in their system. Traditionally, diabetes patients have monitored their glucose levels by sticking their finger with a small lance, allowing a drop of blood to form, and then dipping a test strip into the blood. The test strip is positioned in a handheld monitor that performs an analysis on the blood and visually reports the measured glucose level to the patient. Based upon this reported level, the patient makes critical health decisions on what food to consume, or how much insulin to inject. Although it would be advantageous for the patient to check glucose levels many times throughout the day, many patients fail to adequately monitor their glucose levels due to the pain and inconvenience. As a result, the patient may eat improperly or inject either too much or too little insulin. Either way, the patient has a reduced quality of life and increased risk of doing permanent damage to their health and body. Diabetes is a devastating disease that if not properly controlled can lead to terrible physiological conditions such as kidney failure, skin ulcers, or bleeding in the eyes and eventually blindness, pain and often the amputation of limbs.

Complicating a patient's glucose monitoring, it is known that blood glucose levels can significantly raise or lower quickly, due to several known and unknown causes. Accordingly, a single glucose measurement provides only a brief snapshot of the instantaneous glucose level in a patient's body. Such a single measurement provides little information about how the patient's use of glucose is changing over time, or how the patient reacts to specific dosages of insulin. Accordingly, even a patient that is adhering to a strict schedule of finger pricking and strip testing, the patient will likely be making incorrect decisions as to diet, exercise, and insulin injection. Of course, this is exacerbated by a patient that is less consistent on their strip testing. To give the patient a more complete understanding of their diabetic condition and to get a better therapeutic result, some diabetic patients are now using continuous glucose monitoring.

The CGM sensor is typically temporarily adhered to the patient's skin with an adhesive pad, and the CGM sensor couples to a small housing in which electronics are located. The CGM sensor typically has a disposable applicator device that uses a small introducer needle to deliver the CGM sensor subcutaneously for the patient. Once the CGM sensor is in place, the applicator is discarded, and the electronics housing is attached to the sensor. Although the electronics housing is reusable and may be used for extended periods, the CGM sensor and applicator need to be replaced often, usually every few days.

It will be understood that, depending upon the patient's specific medical needs, that continuous glucose monitoring may be performed at different intervals. For example, some continuous glucose monitors may be set to take multiple readings per minute, whereas in other cases the continuous glucose monitor can be set to take readings every hour or so. It will be understood that a continuous glucose monitor may sense and report glucose readings at different intervals, and the reading rate may change depending on past measurements, time of day, or other criteria.

Electrochemical glucose sensors operate by using electrodes which typically detect an amperometric signal caused by oxidation of enzymes during conversion of glucose to gluconolactone. The amperometric signal can then be correlated to a glucose concentration. Two-electrode (also referred to as two-pole) designs use a working electrode and a reference electrode, where the reference electrode provides a reference against which the working electrode is biased. The reference electrodes essentially complete the electron flow in the electrochemical circuit. Three-electrode (or three-pole) designs have a working electrode, a reference electrode and a counter electrode. The counter electrode replenishes ionic loss at the reference electrode and is part of an ionic circuit.

Unfortunately, the current cost of using a continuous glucose monitor is prohibitive for many patients that could benefit greatly from its use. As described generally above, a continuous glucose monitor has two main components. First, a housing for the electronics, processor, memory, wireless communication, and power. The housing is typically reusable, and reusable over extended periods of time, such as months. This housing then connects or communicates to a disposable CGM sensor that is adhered to the patient's body, which uses an introducer needle to subcutaneously insert the sensor into the patient. This sensor must be replaced, sometimes as often as every three days, and likely at least once every other week. Thus, the cost to purchase new disposable sensors represents a significant financial burden to patients and insurance companies. Because of this, a substantial number of patients that could benefit from continuous glucose monitoring are not able to use such systems and are forced to rely on the less reliable and painful finger stick monitoring.

SUMMARY

In some embodiments, a continuous glucose monitoring sensor includes a working electrode, a reference electrode and a counter electrode. The working electrode has a first wire with a first flat surface and an electrochemical element on the first flat surface. The reference electrode has a second wire with a second flat surface, and the counter electrode has a third wire with a third flat surface. The first wire, the second wire and the third wire serve as sensor wires for the working electrode, the reference electrode and the counter electrode. The second flat surface and the third flat surface face toward each other.

In another embodiment, a novel working electrode is disclosed for use in a continuous biological sensor. The working electrode uses a plastic substrate that is coated with a specially formulated carbon containing compound. This carbon-containing compound is an aqueous dispersion of a carbon material in an elastomeric material. The carbon-compound is applied to the plastic substrate, and then further membranes and coatings are applied to form the working electrode. The working electrode may then be associated with one or more reference electrodes or counter electrodes to form the biological sensor.

In one example, the plastic substrate can be polyethylene, polypropylene, polystyrene, polyvinyl chloride, or polylactic acid, and may be formed into an elongated wire. The carbon material may be, for example, graphene, diamagnetic graphite, pyrolytic graphite, pyrolytic carbon, carbon black, carbon paste, or carbon ink, which is aqueously dispersed in an elastomeric material such as polyurethane, silicone, acrylates or acrylics. Optionally, selected additives may be added to the carbon compound prior to it being layered onto the plastic wire. These additives may, for example, improve electrical conductivity or sensitivity, or act as a catalyst for target analyte molecules.

In one particular application, the plastic substrate is formed into an elongated wire, and is then coated with a carbon compound that has a carbon material aqueously dispersed in an elastomeric material. An additive may be added to the carbon compound that acts as a hydrogen peroxide catalyst, such as Phthalocyanine or Prussian blue. Also, the additive may be in the form of a metal oxide to enhance electrical characteristics, with the preferred metal oxides formed with Copper, Nickel, Rh, or Ir.

Advantageously, a working electrode may be constructed that is durable, strong, flexible and has exceptional electrical and sensitivity characteristics. Further, as the working electrode may be constructed without the use of expensive and rare platinum, a much more cost-effective working electrode can be provided. Such a platinum-free electrode will enable less expensive sensors to be provided to patients, thereby allowing more patients to obtain the substantial benefits of continuous monitoring, and in particular, continuous glucose monitoring. This also allows more flexibility in the mechanical design and construction of sensors. Additionally, this design allows for other analytes/enzymes beyond glucose where many enzymes systems require carbon based electrodes for best performance.

In yet another embodiment, a sensor for a continuous biological monitor is disclosed that has a working electrode with (1) a new interference layer for enhancing and stabilizing the interaction of hydrogen peroxide with a conductor layer and (2) an enhanced glucose limiting layer that is formed of physical hydrogen bonds. Although these inventive aspects may be used independently, they combined to form a highly desirable new working electrode and sensor. The new sensor is easier and less expensive to manufacture than prior devices, and provides improved sensitivity, better linearity and enhanced accuracy. As compared to prior working sensors, the new interference layer more precisely regulates the flow of hydrogen peroxide from an enzyme membrane to its electrical conductor, and enables greater interaction between hydrogen peroxide and the surface of the electrical conductor. The new sensor also has an outer protective glucose limiting layer that is formed using physical hydrogen bonds instead of providing for chemical cross-linking.

In one example of the interference layer, an interference compound is electrodeposited onto a conductive substrate, and the enzyme layer is applied over the interference compound. The interference compound is 1) nonconducting, 2) ion passing, and 3) permselective according to molecular weight. Further, it is electrodeposited in a thin and conformal way, enabling more precise control over the flow of hydrogen peroxide from the enzyme layer to the conductive substrate. In one particular example, the interference material is made by mixing a monomer with a mildly basic buffer, and then electropolymerizing the mixture into a polymer. For example, the monomer may be 2-Aminophenol, 3-Aminophenol, 4-Aminophenol, Aniline, Naphthol, Phenylenediamine, or blends thereof which are mixed with a buffer and electropolymerized into a polymer. It will be appreciated that other monomers may be used. In a more specific example, the monomer is 2-Aminophenol and the buffer is Phosphate Buffered Saline (PBS) at about 8 pH. The monomer and the buffer are mixed and electropolymerized into the polymer Poly-Ortho-Aminophenol (PoAP). The PoAp is then electrodeposited onto the conductive substrate. The permselectivity of the PoAP may be adjusted by the pH of the buffer, for example by adding sodium hydroxide (NaOH).

In one example of the glucose limiting layer, 1) a hydrophilic bonding material, 2) a hydrophobic bonding material, and 3) a solvent are mixed together to form a bonding gel. The bonding gel is then applied over the enzyme membrane layer, and the gel is cured. The hydrophilic material is typically selected to be a high molecular weight, readily dispensable, and provide for strong hydrogen bonding. In one particular example, the hydrophilic bond material is Polyvinylpyrrolidone (PVP). The hydrophobic material is selected to be biocompatible, and to have sufficient hardness and still provide for appropriate interaction with the hydrophilic material and the solvent. It is been found that polyurethane and silicone are desirable hydrophobic materials. Finally, the solvent is selected to be polar, binary and volatile enough to support the curing requirements.

Advantageously, the novel interference layer and the novel glucose limiting layer are both economically manufacturable to provide more cost-effective working electrodes. Further, both new membranes provide for enhanced linearity and overall detection characteristics for the working electrode. In one example, the interference layer is non-electron conducting, ion passing, and is permselective for molecular weight and the glucose limiting layer is a self cross linking formulation of acrylic poly and polyurethane.

In yet another embodiment of the invention, the working wire has an enzyme layer comprising an aqueous emulsion of a polyurethane and GOx blend, which is applied to the working wire and cured. The new enzyme layer has better stability and full entrapment of GOx, a more even dispersion, and enables higher loading of GOx and better overall sensor sensitivity. It will also be understood that for measuring other metabolic functions other enzymes could be substituted for GOx.

In another embodiment of the invention, the working wire has a carbon-enzyme layer comprising an aqueous emulsion of a polyurethane, carbon and GOx blend, which is applied and cured to a plastic substrate for a working wire. The new carbon-enzyme layer has better stability and full entrapment of GOx, a more even dispersion, and enables higher loading of GOx and better overall sensor sensitivity. Further, the carbon-enzyme layer is able to directly generate free electrons in proportion to the amount of glucose reacted, thereby by eliminating any need for expensive platinum. It will also be understood that for measuring other metabolic functions other enzymes could be substituted for GOx.

BRIEF DESCRIPTION OF THE DRAWINGS

These and other objects and advantages of the present disclosure will become apparent upon reading the following detailed description and upon referring to the drawings and claims.

FIG. 1 shows various views of flat-surface electrodes, in accordance with some embodiments.

FIGS. 2A-2D show various views of flat-surface electrodes with a triangular support core wire, in accordance with some embodiments.

DETAILED DESCRIPTION

Figure 3:
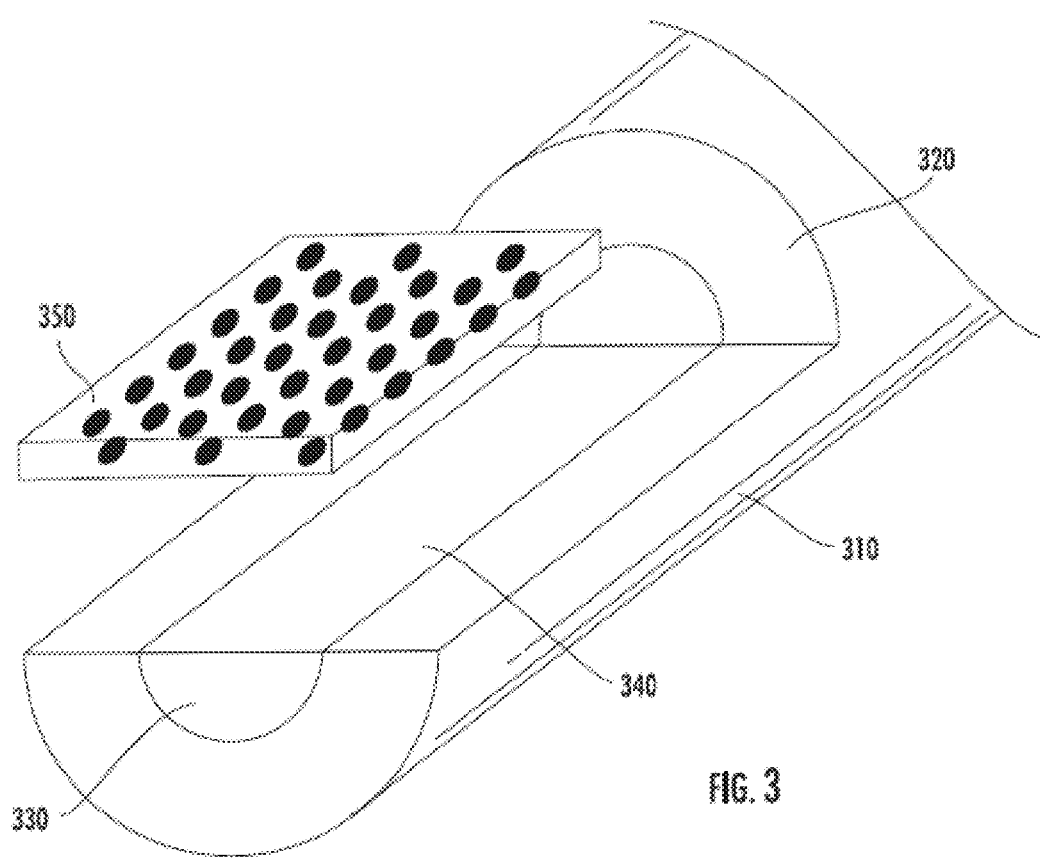
FIG. 3 shows an electrochemical element being mounted to a flat-surface electrode, in accordance with some embodiments.

The present disclosure relates to structures and processes for sensors used in a continuous metabolic monitor, such as a continuous glucose monitor. In particular, the present devices and methods describe novel membranes and substrates for use with a working electrode in a continuous metabolic sensor. Cost can be a prohibiting factor for patients who could benefit from the use of CGMs. Accordingly, there is a significant need in the market for a lower-cost sensor for continuous biological monitors. It will be understood that cost reduction may be obtained by reducing the manufacturing cost of the sensor itself, by increasing the length of time between sensor replacements, or by a combination of both reducing cost and increasing the useful life. By decreasing the cost of sensors for continuous monitoring, more patients could benefit from the increased quality of life and enhanced therapeutic effect of continuous monitoring Most CGM sensor designs are either planar (flat substrate) or wire-based. Planar types are more amenable to use with 3-pole electrochemical designs since simple wire traces and small electrodes can be easily constructed. However, planar types have deficiencies regarding physiology since a planar substrate has some directionality and also has sharp edges due to its geometry, which leads to a more aggressive biologic response to the device. Wire-based systems result in better physiological responses from the patient than planar systems due to the smooth nature of their geometry but have been mostly confined to a single wire for ease of insertion through a needle. This single wire constraint due to the space limitations of needle-based sensor delivery typically limits the designs to 2-pole electrochemical designs. The 2-pole design has an added drawback of making the reference electrode non-renewable and thus the electrode material is consumed to complete the electrochemical circuit, which limits the working life of the system.

A challenge of wire-based sensor designs is making electrical connections on the distal end. The single wire configuration requires in-situ fabrication of working membranes and chemistries and thus limits the approaches and materials that can be used in such designs. Separate wires for working, reference and counter electrodes would be ideal for ease of fabrication; however, this approach is limited by the internal diameter of the insertion needles.

The present embodiments disclose a wire-based 3-pole electrochemical design that solves deficiencies of the aforementioned designs. The working chemistries are made separately from the wires and then bonded to the underlying sensor wires. This allows for lower cost materials and methods since components of the present CGM devices can be made independently from each other. Also, more cost-effective scaled manufacturing is enabled since manufacturing the wires separately does not require 100% sensor quality testing, and quality testing can be performed on a sheet or lot basis. Some embodiments of the disclosed wire-based systems use carbon-based, such as graphene-based, electrodes manufactured in large-scale sheets with working chemistries that are then attached to the working electrode.

Wire-Based 3-Pole Electrode Design

FIG. 1 illustrates an embodiment of a wire-based 3-pole system 100 of a continuous glucose monitoring sensor in which a split wire design is used. In this embodiment, a portion of a wire such as a half-wire is provided for a reference electrode 110 and a counter electrode 120, each having a flat surface across approximately its diameter such that the wires have semi-circular cross-sections. In some embodiments, the flat surface of the reference electrode 110 and the flat surface of the counter electrode 120 face toward each other. Each half-wire electrode, such as the reference electrode 110 and the counter electrode 120, may have a partial surface area such as 82% of the surface area of a full wire having the same diameter, while still allowing the reference and counter electrode assembly to fit within a small diameter insertion needle 102 for insertion under the skin. In other words, the split-wire configuration enables the reference electrode 110 and the counter electrode 120 to provide nearly the same surface area as two full wire electrodes, but only occupy the space of one wire within the insertion needle 102 instead of two full wires. Although half-wires are depicted for the reference electrode 110 and counter electrode 120—where each wire has been split along its diameter along a length of the wire—other partial fractions of the wire may be utilized to form the flat surface electrodes such as, for example, 30% to 70%, or 40% to 60%, typically defined by a chord drawn across the circular cross-section of the wire to get larger percentages of the surface area of full wire.

A working electrode is fabricated by also creating a flat portion on a wire. FIG. 1 shows two embodiments—a 1-sided working electrode 130 and a 2-sided working electrode 135—either of which may be used. The 1-sided working electrode 130 has a semicircular cross-section where half of the wire's cross-sectional area has been removed, while the 2-sided working electrode 135 has a rectangular cross-section where portions of the wire above and below the flat portion have been removed. The portions removed may be equal or one portion—either the top portion or the bottom portion—may be larger than the other. The flat portion(s) of working electrode 130 or 135 is used to support an electrochemical element which is the reactive component that senses glucose in the patient's interstitial fluid.

FIG. 1 also shows insertion of the electrodes into insertion needle 102, where it can be seen that this 3-pole design of the sensor occupies a space within the needle lumen equivalent to only two wires instead of three wires. The working electrode (where 2-sided working electrode 135 is shown in this illustration) utilizes the space of one wire, and the reference electrode 110 and counter electrode 120 together occupy the space of another wire. Diameters of the wires used for the reference electrode 110, counter electrode 120 or working electrode 135 may be, for example, from 0.002 inches to 0.007 inches. The length or surface area of the electrode portions themselves can be tailored according to the desired sensor sensitivity and required design specifications.

Other embodiments of systems in which flat surface electrodes are used in a continuous glucose monitoring sensor are shown in FIGS. 2A-2D. In the radial cross-sectional views of designs 200 (FIG. 2A) and 210 (FIG. 2B), compact systems are assembled from a support core wire 140 having a triangular cross-section surrounded by working electrode 135, reference electrode 110 and counter electrode 120 facing the flat surfaces of the triangular core wire 140. Each of the wires for the working electrode 135, reference electrode 110 and counter electrode 120 have flat surfaces that are positioned to be facing a surface of the triangular-shaped core wire 140. As shown in FIGS. 2A-2B, the reference electrode 110 and counter electrode 120 are approximately semi-circular in cross-section, while the working electrode 135 can be semicircular (design 200 of FIG. 2A) or rectangular (design 210 of FIG. 2B) in cross-section. Schematics 220 (FIG. 2C) and 230 (FIG. 2D) provide a longitudinal cross-sectional view and a perspective view, respectively, of the end of the triangular support wire, showing that this triangular design can be a completely self-inserting sensor. That is, a tip 142 of the triangular core wire 140 may be sharpened to a point, or pointed, such that the sensor can be inserted directly, without requiring the use of a needle to place the sensor within the subcutaneous tissue.

The flat surfaces of the electrodes in these various embodiments provide support for fragile electrochemistry materials, such as a carbon-based sheet which is typically brittle. In one example, a support sheet (e.g., made of pyrrole or polyaniline) can be created, and then a carbon material is deposited onto the support sheet. The support sheet provides a substrate to which the carbon bonds well, and also should be conductive to electrically couple the electrochemical (e.g., carbon/pyrrole) sheet to the electrode wire. The conductive sheet material can then be impregnated or coated with sensing chemistries via various drawn membrane or spin coating techniques.

The electrochemistry material sheet can be made separately from the electrode wire, and then mounted on the flat surface of the electrode as shown in FIG. 3. In this example of FIG. 3, a wire 310 having insulation 320 surrounding a conductive wire core 330 has a portion of its end removed to form a flat surface 340. A carbon or carbon/graphene/pyrrole sheet 350 is cut to size and placed on the flat surface 340 of the flat electrode wire 310. For example, once the flat sheets are fabricated with sensing chemistries, these sheets 350 can be laser cut into small portions and then assembled onto the flat surface 340 of the wire 310.

The support sheet can be made by, for example, depositing a pyrrole layer to make electrical contact to the flat surface of the electrode. In other embodiments, an electropolymerization of additional pyrrole can be used to connect the electrode metal to the sheet, or conductive adhesives or other electrical contact bonding methods can be used to make electrical contact as well.

In other embodiments, the electrochemistry components can be formed in-situ on the electrode instead of forming a sheet separately from the electrode. For example, an alternative fabrication method for in-situ creation of sensing chemistry and membrane may include pad or screen printing, painting, or 3D-printing directly onto the flat plane(s) of the wire.

The carbon material can be in the form of, for example, an ink or a paste, and the carbon can include various allotropes such as but not limited to graphite, graphene, fullerenes, and/or nanotubes. Materials other than pure carbon can be used, including platinum black, carbon platinum pastes, carbon gold pastes or other known working electrode surface materials, alone or in combination (e.g., carbon, platinum, gold, palladium, rhodium, iridium). In some embodiments, high surface area nano-porous materials of graphene and/or other nanomaterials can be used, to increase the number of active chemical sites available for reactions.

Carbons are lower cost than the metals that are typically used for biocompatible applications (e.g., gold and platinum). However, due to the inherent brittle nature of carbon materials, carbon-based electrodes have been conventionally used in planar style electrodes (such as finger sticks) where the carbon can be supported by the planar substrate without applying undue mechanical loads on the electrode. The present embodiments overcome the difficulties of using carbon-based materials on a wire electrode by providing the mechanical support required for the carbon material and by eliminating the typical need for in-situ fabrication of the working chemistries on the wire (although in-situ fabrication may be used).

After the sensing chemistry has been created on the electrode, whether separately or in-situ, a final dip coating may be used to seal the entire system using hoop strength created by polymer shrinkage upon drying. This final polymer layer also serves as a biocompatible and glucose limiting membrane required for creating a linear glucose response, and provides the biosafety required for an implanted sensor.

The present flat-wire embodiments may also be used to optimize the electrochemical substrate so that it can be tuned for direct electron transfer chemistries by keeping the redox center close to the porous carbon surface or within encapsulating polymers. One such embodiment uses an aminophenol covalently bonded to the carbon electrode by electrografting and is subsequently linked by diazonium chemistry to glucose oxidase (GOx) to provide direct electron transfer. Embodiments can be directly used with conductive polymers (e.g., PEDOT-PSS, poly-pyrroles, polyanilines, naphthol, phenylenediamine, etc.) formed in-situ on a porous carbon sheet that would work with normal enzymes (either glucose oxidase (GOx) or glucose dehydrogenase (GDH)) and/or enzymes with a mediator to create hybrid enzyme systems that alter the need for high bias voltages and thus reduce interferences from all sources.

In some embodiments, a redox enzyme can be immobilized on the electrode surface in a new manner such that direct electron transfer between the active side of the enzyme and the transducer is possible. The major unique character of such embodiments of an amperometric glucose sensor is that its biased potential is in the range of 0 to −0.5V, ideally to be around −0.1V. In comparison, a conventional CGM sensor has a biased potential of typically +0.55V. There are two major methods to achieve the lower biased potential of the present designs. A first method is an in-situ electro-polymerization of a conductive polymer with a redox enzyme. The sensing layer is formed by applying potential cycles or sequences of suitable potential pulses with the enzyme and monomer/comonomers solution. An advantage of this approach is that the films are formed exclusively on the electrode surfaces due to the electrochemical initiation of the deposition process. A second method is the incorporation of a redox mediator into the polymers or the prepolymer. The polymer that contains the redox mediator can be physically mixed with the enzyme, then be deposited onto the electrodes through dip coating, spin coating or other coating methods. This can also be achieved through the in-situ polymerization of the redox-mediator-containing prepolymer with other active prepolymers in the presence of the enzyme solution and the electrodes. The resulting sensing layer on the electrode contains the matrixed enzyme inside the polymer network with the covalently linked redox mediator.

Carbon Substrate

In some embodiments, a cost-effective platinum-free sensor is used in a continuous biological monitoring system. Embodiments provide for a substantial reduction in cost for the manufacture of the working electrode for such a biological sensor. Although the embodiments are discussed primarily for the use in continuous glucose monitoring, it will be understood that many other uses for biological sensing exist that would benefit from a reduced cost sensor and working electrode.

Typically, a sensor for a continuous biological monitoring system has a working electrode and a reference electrode. The working electrode and reference electrode are constructed and arranged such that they can sense the concentration of an analyte in the patient, oftentimes by measuring a concentration or ion flow within the blood or other body fluids, such as interstitial fluid (ISF). It will be understood that a sensor may include multiple working wires, multiple reference electrodes, and counter electrodes.

Generally a working electrode needs to be constructed to meet three basic requirements. First, it must be strong enough to withstand insertion under the patient's skin and to withstand the vibrations, shocks, and motions during use. Second, it needs to be flexible enough to follow a curved path into the skin, and to allow for some movement after insertion for patient comfort. And third, it needs to provide the electrical characteristics to support consistent and accurate sensing. Accordingly, known working electrodes typically use some form of a platinum wire, either a solid platinum wire, or a less expensive metal material (such as tantalum) coated with platinum. It is this reliance and use of platinum that drives some of the high cost of current biological sensors.

Advantageously, embodiments of the present disclosure eliminate the need for expensive and rare platinum to make a working electrode that not only has sufficient mechanical strength and flexibility but has superior electrical and sensing characteristics. Further, embodiments of the present working electrodes are constructed of materials known to be safe in a human body. This also allows for the use of alternative geometries of sensors and different styles of sensor manufacturing.

In one particularly cost-effective embodiment, the working electrode uses a plastic material as a substrate. The plastic material is sufficiently strong to support insertion into human body, while having the needed flexibility for insertion and patient comfort. This plastic substrate can be formed into an elongated wire in many shapes to support construction of different types of sensors. The plastic wire may then be coated with a specially formed carbon compound. Plastic wire has the added advantage of improved fatigue performance in comparison to a metallic wire of the same dimension. Traditionally, elemental carbon paste electrodes could not be considered for use on a flexible working electrode, as carbon is highly brittle and needed to be rigidly supported. Also, carbon paste electrodes are usually water-soluble, and therefore dissolve and degrade when inserted into a wet environment. And finally, carbon has a high electrical resistance compared to platinum metal, and therefore is not practically usable as a conductor in a biological sensor. However, the new forms of carbons in a carrier compound used over the plastic wire as disclosed herein overcome the several disadvantages of the elemental carbon.

In some embodiments, a carbon compound is prepared as a coating that is an aqueous dispersion of a carbon material with an elastomeric material. For example, the carbon material may be in the form of graphene, diamagnetic graphite, pyrolytic graphite, pyrolytic carbon, carbon black, carbon paste, or carbon ink. In some cases, to support particular applications, other additives may be added to the carbon compound for enhanced electrical and response characteristics. For example, a hydrogen peroxide catalyst could be added to the carbon compound to support enhanced glucose level sensitivity. It will be understood that other sensing molecules may be used for other sensing applications.

The carbon compound, as described above, is then applied to the plastic wire. Most often, this would be through a simple dipping process, although it will be understood that the coating could also be sprayed, extruded, deposited, or even printed onto the plastic wire or direct 3-D printed substrates. The coated wire may then be processed into a working electrode using known processes by adding membranes, associating it with a reference electrode, and adding protective biological coatings.

Figure 4A:
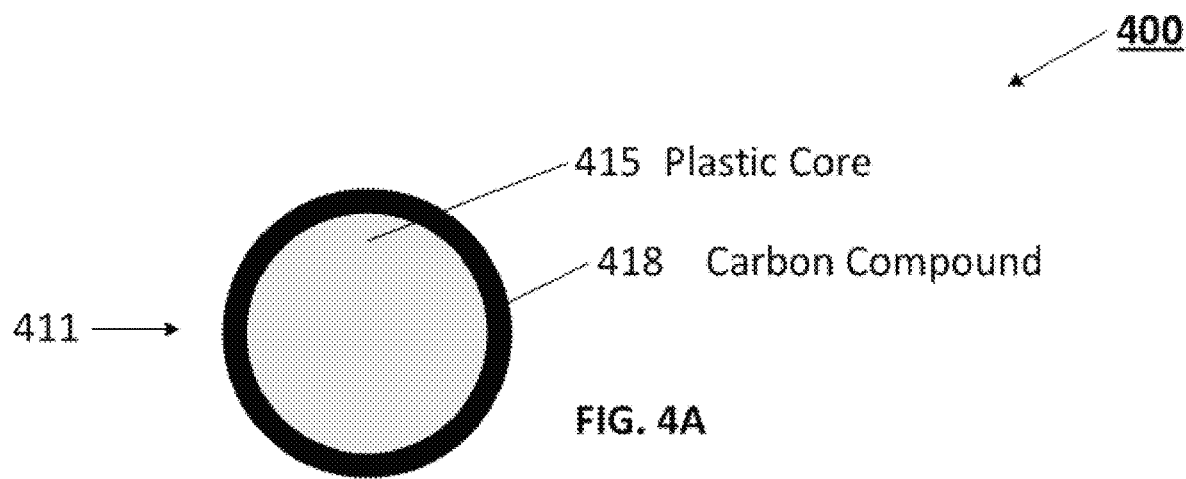
FIG. 4A is a not-to-scale illustration of a carbon coated wire for a working electrode in accordance with some embodiments.
Figure 4B:
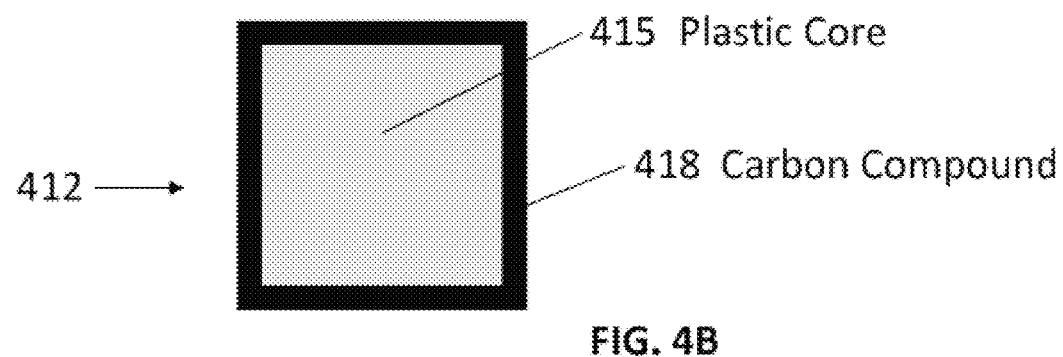
FIG. 4B is a not-to-scale illustration of a carbon coated wire for a working electrode in accordance with some embodiments.
Figure 4C:
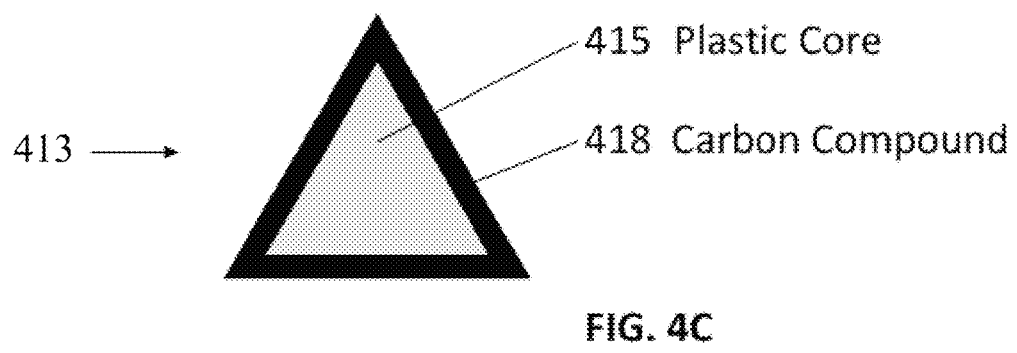
FIG. 4C is a not-to-scale illustration of a carbon coated wire for a working electrode in accordance with some embodiments

Referring now to FIG. 4A, FIG. 4B, and FIG. 4C, carbon coated wires 400 are illustrated. The carbon-coated wires 400 include wire 411 in FIG. 4A, wire 412 in FIG. 4B and wire 413 in FIG. 4C. These illustrations are not to scale and are used only for descriptive purposes. The carbon coated wires 400 each have a plastic core 415 which is fully surrounded by a carbon compound 418. It will be understood that the plastic core 415 may be formed into many different elongated physical shapes. For example, as illustrated in FIG. 4A, the plastic core 415 may have a circular cross-section. As illustrated in FIG. 4B, the plastic core 415 may have a rectangular or square cross-section. And as illustrated in FIG. 4C, the plastic core 415 may have a triangular cross-section. It will be appreciated that many other cross-section shapes may be used.

The carbon compound 418 is formulated to have superior electrical characteristics appropriate mechanical characteristics such as strength and flexibility, and to be cost-effective. For example, a standard carbon conductive ink has a resistivity of about 23 Ohm/mm$^2$, while carbon compound 418 can be formulated to have a much more desirable resistivity such as 1-5 Ohm/mm$^2$. In this way, the carbon compound 418 has been found to have resistivity that is an order of magnitude lower than standard carbon conductive inks, dramatically increasing its utility and performance as a conductor for working wire. Not only is the carbon coating 418 far less expensive than platinum, it is also easier and more cost-effective to apply as a coating. For example, the carbon compound 418 may be used with a low-cost dipping, spraying, extrusion, depositing, or printing process. It will be understood that the carbon coated wires 400 will be further processed to add membranes and protective coatings according to the specific application, and that they will be associated with one or more reference or counter electrodes. It will be understood that the association of the working wire with a reference wire may be accomplished in several ways. For example, the working wire and the reference wire may be placed side-by-side, formed concentrically, wrapped into a twisted relationship, layered, or formed into any other known physical relationships for a working wire and its associated reference wire.

In one example, the carbon coating may be formulated as follows. It will be appreciated that many other formulations fall within the teachings herein.

Figure 5:
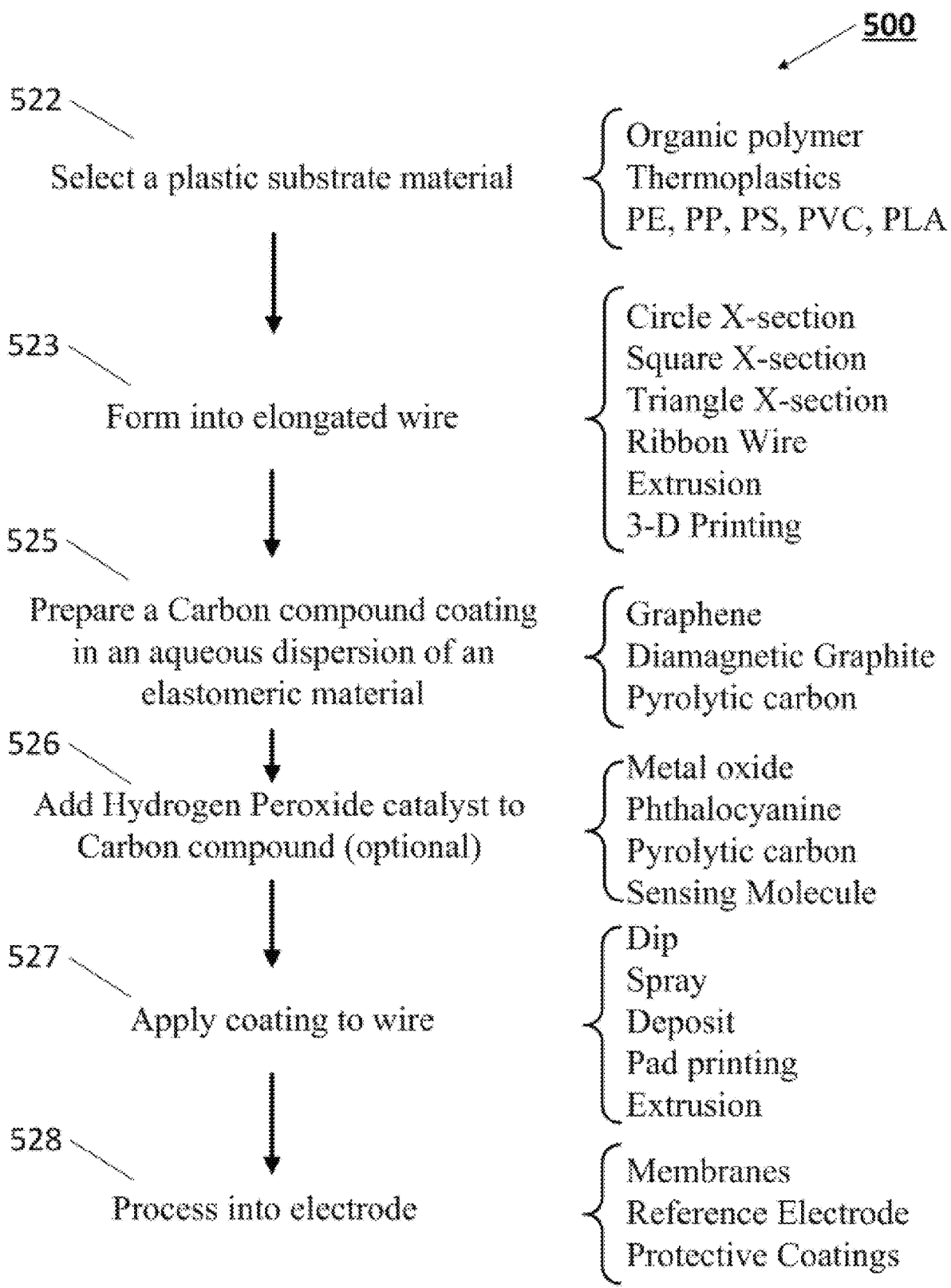
FIG. 5 is a flowchart of general manufacturing steps for making a working electrode in accordance with some embodiments.

Formulation (% by weight for a total of 100%)
    an aqueous dispersion, comprising
        40-60% Polyurethane (i.e. Hauthaway HD4661,
        40-60% Acrylic Polyol (i.e. Acquathane),
        0.5-5%% Polyvinylpyrrolidone).
    0.1-0.5% Carbon Black
    0.05%-0.5% Graphene
    0.1-0.5% Pyrolytic Graphite
    0-10% additional water Referring now to FIG. 5, a process 500 for making a carbon working electrode is illustrated. Process 500 begins with selecting a plastic substrate material in step 522. This plastic substrate material is selected to have sufficient strength for being inserted under the skin of a patient, as well as flexibility for patient comfort and ease of manufacturing. Further, it will be understood that the plastic substrate should be biologically safe and generally electrically unreactive. It will be understood that a wide range of materials meet the mechanical and functional requirements for the selected plastic substrate. For example, numerous organic polymers and thermoplastics may be used. For illustrative purposes only, the following specific plastic substrate materials may be used: polyethylene, polypropylene, polystyrene, polyvinyl chloride, and polylactic acid. It will be appreciated that a wide variety of materials may be used as the plastic substrate.

The selected plastic substrate material is then formed into an elongated plastic wire in step 523. It will be understood that the wire may take many cross-sectional shapes, such as circular, square or triangular. Generally, these wires may be formed using well-known extrusion processes. The plastic substrate could also be formed into a ribbon wire, or in some cases manufactured by printing such as 3D printing.

A carbon compound is prepared in step 525 for application to the plastic substrate. The carbon compound has a carbon material that is aqueously dispersed in an elastomeric material. The elastomeric material is selected for its mechanical properties, such as strength and flexibility, while the carbon material is selected for an advantageous electrical property. There are several acceptable elastomeric materials that may provide the desired characteristics, for example: as polyurethane, silicone, acrylates or acrylics. It will be understood that other elastomeric materials may be substituted. Experimental results related to the present disclosure have shown that the carbon compound, after the elastomeric material is cured, does not delaminate from the plastic wire, in contrast to platinum coated of a Tantalum wire.

The carbon material in the carbon compound is selected for enhanced electrical characteristics. For example, as briefly discussed above, elemental carbon has much too high an electrical resistance to be effectively used in a working electrode. However, with the addition of graphene, diamagnetic graphite, or pyrolytic carbon, the carbon compound can be formulated to have advantageous electrical characteristics. Indeed, the loading of the carbon material with the elastomeric material can be adjusted to create a carbon compound with a desired resistance, for example 100 ohms/$cm^2$ or less. In this way, a working electrode using such a carbon compound coating can be used such that the sensing system has a highly desirable signal-to-noise ratio. Elemental carbon would not be able to enable such a signal-to-noise ratio due to the high electrical background from the high resistance of carbon electrodes.

Optionally, an additional catalyst or material may be added to the carbon compound in step 526 to enhance electrical or sensing characteristics. For example, metal oxides may be added to the carbon compound for reducing resistivity thereby enabling a working electrode with a higher signal-to-noise ratio capability as compared to elemental carbon. For example, in some embodiments metal oxides of nickel or copper may be used. In some embodiments, metal oxides of Rh and Ir, when added to the carbon compound, can enable the working wire to operate with a lower bias voltage as compared to a wire formed with platinum. By operating at a lower bias voltage, a working wire is enabled to operate with greater sensitivity, and with a lower power consumption.

In another example of an additive in step 526, a catalyst for hydrogen peroxide may be added to the carbon compound. In one example, phthalocyanine or Prussian blue is added to the carbon compound, thereby substantially increasing the sensitivity of the working wire to hydrogen peroxide, which is highly advantageous to the overall accuracy and sensitivity for a glucose monitor sensor. It will be understood that other hydrogen peroxide catalysts may be used. Also, for working wires intended for biological sensing other than glucose, it will be understood that other sensing molecules and molecule catalysts may be used.

The coating can then be applied to the plastic wire substrate in step 527. As the carbon compound is inexpensive and easy to work with, the plastic substrate may be dipped into the carbon compound. For other applications, the carbon compound may be sprayed onto the plastic wire, may be deposited using well-known deposition processes, co-extrusion, or may be applied using a printing process, such as pad printing. It could also be made to 3-D printed. It will be understood that any appropriate application process may be used to coat or deposit the carbon compound onto the plastic substrate. The carbon compound coating then cures prior to further processing.

Once the carbon coated working wire has cured, it may be processed into a working electrode in step 528. In this way, membranes and protective coatings may be added, and the working wire is associated with one or more reference or counter electrodes. The processes for adding membranes, protective coatings, and associating with other electrodes is well known, so will not be described herein. For example, working electrodes and reference electrodes may be set side to side, layered, concentrically formed, or wrapped together. It will also be understood that some applications will use multiple working electrodes, multiple reference electrodes, or counter electrodes.

Due to the aqueous nature of the carbon containing compound, enzymes or other sensing molecules and chemistries could be included directly in to the carbon containing compound, improving efficiency of the electron transfer and further improving signal to noise ratios by removing additional layers and diffusional distances. This incorporation of enzymes and other sensing chemistries into the sensor wire itself would also further simplify manufacture of these sensors.

Figure 6:
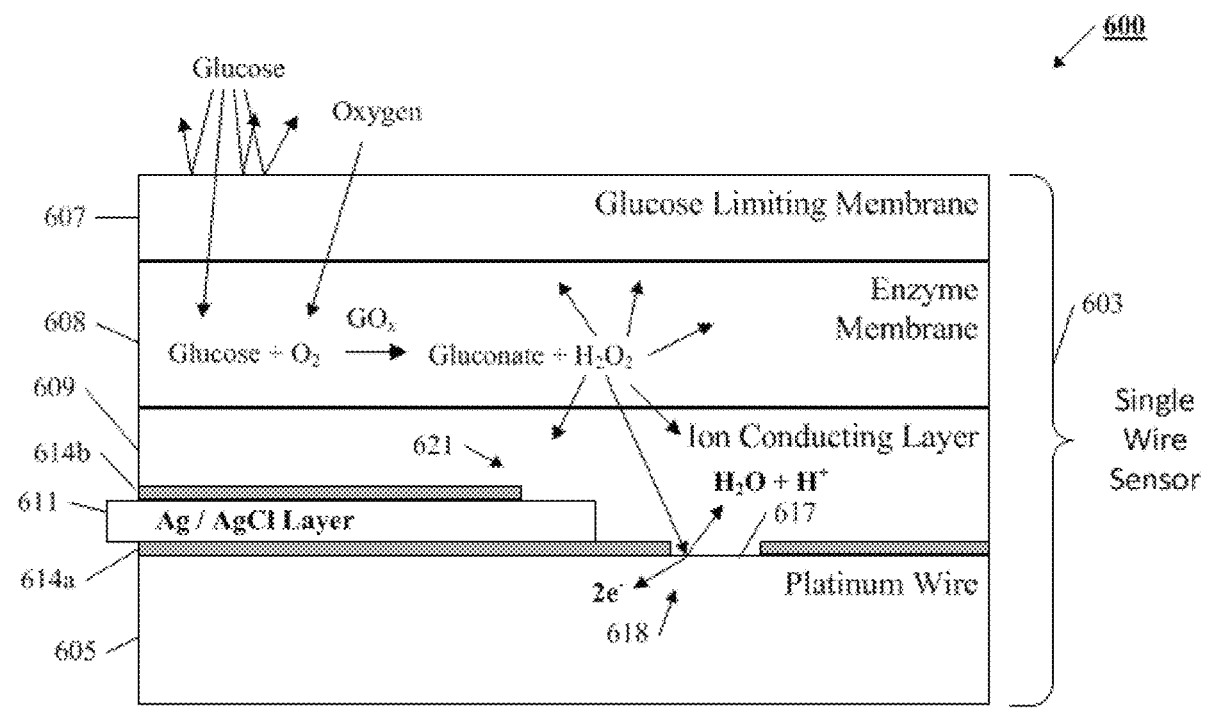
FIG. 6 is a not-to-scale cross-sectional block diagram of a prior art single wire sensor.

Referring now to FIG. 6, a prior art single wire sensor 600 for a continuous biological monitor is illustrated. Those skilled in the art will recognize that sensor 600 is a high level diagram for instructional purposes only, and has left out substantial detail to facilitate improved understanding. As is understood, such a prior art sensor will integrate both the function of a working electrode and a function of a reference electrode on a single wire. It will be understood that a single wire electrode may be constructed with multiple working electrode layers and with multiple reference electrode layers. A single wire electrode may also use or be supplemented with a counter electrode. Although sensor 600 is illustrated as a wire with concentrically formed layers, it will be understood that the other physical implementations may be used, such as layered, spiraled, flat, and other well-known physical relationships.

The prior art sensor 600 has an elongated conducting wire 605, which is often made of solid platinum or a platinum coating on a less expensive metal or plastic substrate. It will be appreciated that other types of conducting wires may be substituted. The conducting wire 605 is wrapped with an electrically insulating layer 614a. A band 618 of the insulating layer 614a is removed during manufacturing that exposes a portion 617 of the platinum wire, which remains uninsulated. The removal of this band 618 must be done very accurately and precisely, as this affects the overall electrical sensitivity of the sensor 600. For example, this band 618 may be in the order of 20 μm thick, and must be cut to about 40 μm, although other thicknesses and widths may be used depending upon the overall structure of the sensor 600.

A layer 611 of silver or silver chloride is positioned around the electrically insulating layer 614, and a second layer of electrically insulating material 614b is disposed around the silver/silver chloride layer 611. During manufacture, a portion 621 of the silver/silver chloride layer 611 needs to be exposed. Typically, this requires precise removal of a small portion of layer 614b using, for example, a laser ablation process. A second removal process may also be used at the connection end of the sensor 600 to expose a small portion of the silver/silver chloride layer 611 so that a more convenient electrical connection may be made. Removal of the insulating layers from the silver/silver chloride layer 611 is a precision operation, as the layer may be in the order of only 20 μm thick. This expensive removal operation adds substantial cost and manufacturing risk to making the single wire sensor 603.

In operation, the glucose limiting membrane 607 substantially limits the amount of glucose that can reach the enzyme membrane 608. By limiting the amount of glucose that can reach the enzyme membrane 608, linearity of the overall response is improved. The glucose limiting membrane 607 also permits oxygen to travel to the enzyme membrane 608. The key chemical processes for glucose detection occur within the enzyme membrane 608. Typically, the enzyme membrane 608 has one or more glucose oxidase enzymes (GOx) dispersed within the enzyme membrane 608. When a molecule of glucose and a molecule of oxygen ($O_2$) are combined in the presence of the glucose oxidase, a molecule of gluconate and a molecule of hydrogen peroxide ($H_2O_2$) are formed. The hydrogen peroxide then generally disperses both within the enzyme membrane 608 and into the ion conducting layer 609.

At least some of the hydrogen peroxide travels to the window (band 618) in the electrically insulating layer 614a, where it comes into contact with the exposed portion 617 of the platinum wire 605. The platinum surface facilitates a reaction wherein the hydrogen peroxide reacts to produce water and hydrogen ions which are released into the ion conducting layer 609, and two electrons are generated. The electrons are drawn into the platinum wire 605 by a bias voltage placed across the platinum wire 605 and the silver/silver chloride layer 611. Positive ions from the silver/silver chloride layer 611 are released into the ion conducting layer 609 to complete the electrical circuit. In this way, the magnitude of the electrical current on the platinum wire is intended to be related to the number of hydrogen peroxide reactions, which is intended to be related to the number of glucose molecules oxidized. In this way, a measurement of the electrical current on the platinum wire is intended to be associated with a particular level of glucose in the patient's blood or ISF.

Unfortunately, since the platinum surface (portion 617) has been exposed during the manufacturing process, an oxidation layer has formed in the window 618. This oxidation layer poisons the electrode and interferes with the exposed platinum's efficiency in converting the hydrogen peroxide. That is, the actual useful exposed area of the exposed portion 617 of the platinum wire is substantially reduced by oxidation contamination, which also may lead to unpredictable and undesirable sensitivity results. In order to overcome this deficiency, the single wire sensor 603 must be subjected to sophisticated calibration. Further, the bias voltage between the platinum wire 605 and the silver/silver chloride layer 611 must be set relatively high, for example between 0.4-1.0 V. Such a high bias voltage is required to draw the electrons into the platinum wire, but also acts to attract contaminants from the blood or ISF into the sensor. These contaminants such as acetaminophen and uric acid interfere with the chemical reactions, leading to false and misleading glucose level readings. The single wire sensor 603 is also expensive to manufacture, due in part to the precise laser ablation needed to expose the band 618 in the platinum wire 605, as well as exposing the small 621 portion of the silver/silver chloride layer 611.

Embodiments of the present disclosure are directed to a cost-effective sensor for use in a continuous biological monitoring system. Embodiments provide for a substantial reduction in cost for the manufacture of the working electrode for such a biological sensor. Although the embodiments are discussed primarily for the use in continuous glucose monitoring, it will be understood that many other uses for biological sensors exist that would benefit from a reduced cost sensor and working electrodes with enhanced functionality.

Generally, a sensor for a continuous biological monitoring system is constructed as a two-wire continuous biological sensor that has a working electrode and a reference electrode. The working electrode and reference electrode are constructed and arranged such that they can sense the concentration of an analyte in a patient, oftentimes by measuring concentration molecules, such as glucose, within the blood or other body fluid, such as ISF. It will be understood that a sensor may include multiple working wires, multiple reference electrodes, and counter electrodes.

Interference Layer

Figure 7A:
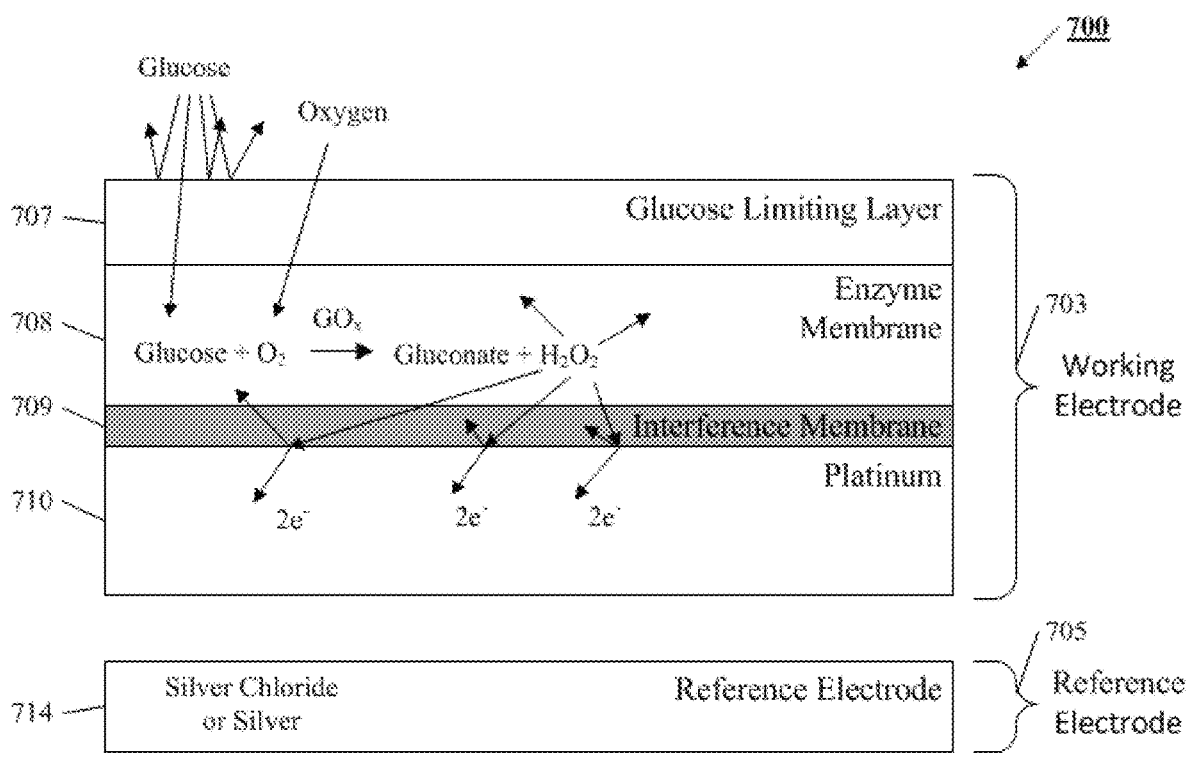
FIG. 7A is a not-to-scale cross-sectional block diagram of a 2-wire sensor having an interference membrane layer in accordance with some embodiments.

Referring now to FIG. 7A, a sensor 700 for a continuous biological monitor is generally illustrated. The sensor 700 has a working electrode 703 which cooperates with a reference electrode 705 to provide an electrochemical reaction that can be used to determine glucose levels in a patient's blood or ISF. Although electrode sensor 700 is illustrated with one working electrode 703 and one reference electrode 705, it will be understood that some alternative sensors may use multiple working electrodes, multiple reference electrodes, and counter electrodes. It will also be understood that sensor 700 may have different physical relationships between the working electrode 703 and the reference electrode 705. For example, the working electrode 703 and the reference electrode 705 may be arranged in layers, spiraled, arranged concentrically, or side-by-side. It will be understood that many other physical arrangements may be consistent with the disclosures herein.

The working electrode 703 has a conductive portion, which is illustrated for sensor 700 as conductive wire 710. This conductive wire 710 can be for example, solid platinum, a platinum coating on a less expensive metal or plastic, or as disclosed above, the conductive wire 710 may be a carbon compound coating on a plastic substrate. It will be understood that other electron conductors may be used consistent with this disclosure. As with prior art working electrodes, working electrode 703 has a glucose limiting layer 707, which may be used to limit contaminations and the amount of glucose that is received into the enzyme membrane 708.

In operation, the glucose limiting membrane 707 substantially limits the amount of glucose that can reach the enzyme membrane 708, for example only allowing about 1 of 1000 glucose molecules to pass. By strictly limiting the amount of glucose that can reach the enzyme membrane 708, linearity of the overall response is improved. The glucose limiting membrane 707 also permits oxygen to travel to the enzyme membrane 708. The key chemical processes for glucose detection occur within the enzyme membrane 708. Typically, the enzyme membrane 708 has one or more glucose oxidase enzymes (GOx) dispersed within the enzyme membrane 708. When a molecule of glucose and a molecule of oxygen ($O_2$) are combined in the presence of the glucose oxidase, a molecule of gluconate and a molecule of hydrogen peroxide are formed. The hydrogen peroxide then generally disperses both within the enzyme membrane 708 and into interference membrane 709.

The interference membrane 709 is layered between the electrical conducting wire 710 and the enzyme membrane 708 in working electrode 703. As will be discussed in more detail below, the interference membrane 709 can be uniquely formulated to have a more precise regulation, compared to conventional insulating layers (e.g. layers 614a/b with Ag/AgCl layer 611 of FIG. 6), of the level of hydrogen peroxide molecules that are enabled to pass from the enzyme membrane layer 708 to a more expansive surface area of the conductive wire 710. This interference membrane 709 may be electrodeposited onto the electrical conducting wire 710 in a very consistent and conformal way, thus reducing manufacturing costs as well as providing a more controllable and repeatable layer formation. The interference membrane 709 is nonconducting of electrons, but will pass negative ions at a preselected rate. Further, the interference membrane 709 may be formulated to be permselective for particular molecules. In one example, the interference membrane 709 is formulated and deposited in a way to restrict the passage of larger molecules, which may act as contaminants to degrade the conducting layer 710, or that may interfere with the electrical detection and transmission processes.

Advantageously, the interference membrane 709 provides reduced manufacturing costs as compared to known insulation layers, and is enabled to more precisely regulate the passage of hydrogen peroxide molecules to a wide surface area of the underlying conductive layer 710. Further, formulation of the interference membrane 709 may be customized to allow for restricting or denying the passage of certain molecules to underlying layers, for example, restricting or denying the passage of large molecules or of particular target molecules.

Interference membrane 709 is a solid coating surrounding the platinum wire 710. In this way, the expense and uncertainty of providing a window through an insulating layer is avoided. Accordingly, the interference membrane 709 may be precisely coated or deposited over the platinum wire 710 in a way that has a predictable and consistent passage of hydrogen peroxide. Further, the allowable area of interaction between the hydrogen peroxide and the surface of the platinum wire 710 is dramatically increased, as the interaction may occur anyplace along the platinum wire 710. In this way, the interference membrane 709 enables and increased level of interaction between the hydrogen peroxide molecules in the surface of the platinum wire 710 such that the production of electrons is substantially amplified over prior art working electrodes. In this way, the interference membrane enables the sensor to operate at a higher electron current, reducing the senor's susceptibility to noise and interference from contaminants, and further enabling the use of less sophisticated and less precise electronics in the housing. In one non-limiting example, the ability to operate at a higher electron flow allows the sensor's electronics to use more standard operational amplifiers (op-amp), rather than the expensive precision op-amps required for prior art sensor systems. The resulting improved signal to noise ratio allows enable simplified filtering as well as streamlined calibration.

Further, during the manufacturing process it is possible to remove oxidation on the outer surfaces of the platinum wire 710 prior to depositing the interference membrane 709. Since the interference membrane 709 acts to seal the platinum wire 710, the level of oxidation can be dramatically reduced, again allowing for a larger interaction surface and further amplification of the glucose signal, resulting in higher electron flow and enabling a higher signal to noise ratio. In this way, the new interference layer prevents fouling of the platinum's electrical interface by eliminating undesirable oxidative effects.

In some embodiments, the interference membrane 709 is nonconductive of electrons, but is conductive of ions. In practice, a particularly effective interference membrane may be constructed using, for example, Poly-Ortho-Aminophenol (PoAP). PoAP may be deposited onto the platinum wire 710 using an electrodeposition process, at a thickness that can be precisely controlled to enable a predictable level of hydrogen peroxide to pass through the interference membrane 709 to the platinum electrode 710. Further, the pH level of the PoAP may be adjusted to set a desirable permselectivity for the interference membrane 709. For example, the pH may be advantageously adjusted to significantly block the passage of larger molecules such as acetaminophen, thereby reducing contaminants that can reach the platinum wire 710. It will be understood that other materials may be used, for example, polyaniline, naphthol or polyethelenediamine.

Sensor 700 also has a reference electrode 705 separate from working electrode 703. In this way, the manufacture of the working electrode is simplified and can be performed with a consistency that contributes to dramatically improved stability and performance. The reference electrode 705 is constructed of silver or silver chloride 714.

Figure 7B:
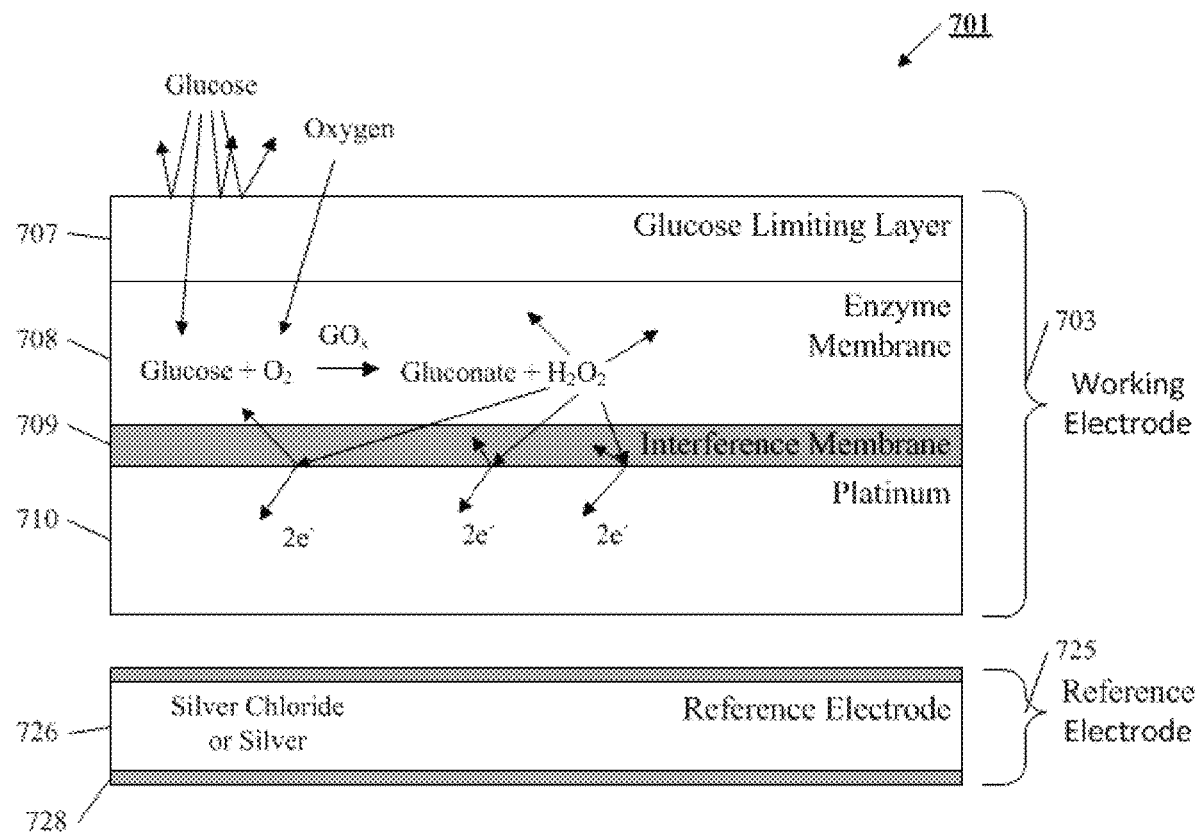
FIG. 7B is a not-to-scale cross-sectional block diagram of a 2-wire sensor having an interference membrane layer and a coated reference electrode in accordance with some embodiments.

Referring now to FIG. 7B, another sensor 701 for a continuous biological monitor is illustrated. Sensor 701 is similar to sensor 700, so will not be described in detail. Sensor 701 has the same working electrode 703 as described with reference to sensor 700. However, sensor 701 has a reference wire 725 that has a silver/silver chloride layer 726 surrounded by an ion limiting membrane 728. The application of this ion limiting membrane 728 over the silver/silver chloride layer 726 desirably controls the current sensitivity of the overall sensor device 701 by controlling the flow of ions from the silver/silver chloride layer 726. In this way, current sensitivity may be advantageously controlled and defined. As will be understood, this can also act as a secondary method to control sensor sensitivity by controlling the chloride release from the electrode's surface.

Figure 8:
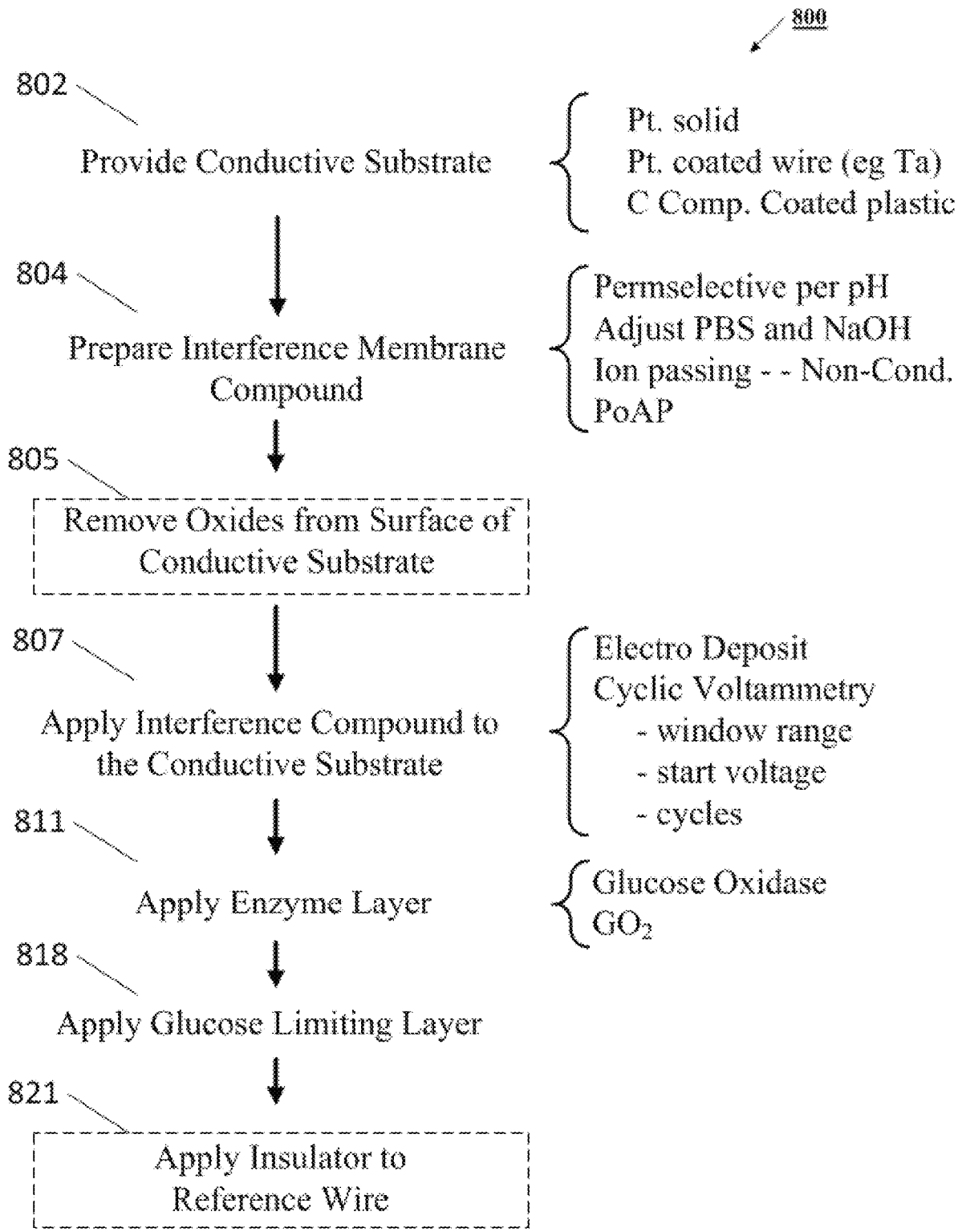
FIG. 8 is a flowchart of general manufacturing steps for making a 2-wire sensor having an interference membrane layer in accordance with some embodiments.

Referring now to FIG. 8, a general description of a process 800 for formulating and applying the interference membrane is illustrated. As shown in step 802, a conductive substrate is provided. This conductive substrate may be in the form of an elongated wire, but it will be appreciated that the conductive substrate can be provided in other forms, such as printed or in the form of conductive pads. In some embodiments, the conductive substrate is a solid platinum wire, a less expensive wire that has been coated with platinum, or as disclosed herein, the conductive substrate may be a conductive carbon compound coated on a plastic substrate. It will be appreciated that other conductive substrates may be used.

As shown in step 804, the interference membrane compound is now prepared. This compound is formulated to be 1) non-electrically conducting; 2) ion passing; and 3) permselective. Further, the compound is particularly formulated to be electrodeposited in a thin and uniform layer, and that has a thickness that is self-limiting due to the nature of electrically driven cross-linking. In this way, the compound may be applied in a way that provides a well-controlled regulation of hydrogen peroxide molecule passage using a simple and cost-effective manufacturing processes. Further, the passage of the hydrogen peroxide can occur over a much larger surface area as compared to prior art working wires.

Generally, the characteristics of the present interference membranes identified above can be formulated by mixing a monomer with a mildly basic buffer, and converting the monomer into a more stable and usable polymer by applying an electropolymerization process. In one formulation:
  a) Monomer: e.g., 2-Aminophenol, 3-Aminophenol, 4-Aminophenol, Aniline, Naphthol, phenylenediamine, or blends thereof.
  b) Buffer: e.g., Phosphate Buffered Saline (PBS) tuned to about 7.5 to about 10 pH, such as 7.5 to 9 pH, such as 8 pH by adding Sodium Hydroxide.
  c) Mix the monomer and buffer and electropolymerize.
  d) Create a polymer; e.g., Poly-Ortho-Aminophenol (PoAP).

In the particular formulation set out above, the 2-Aminophenol monomer is mixed with a PBS buffer being mildly basic at a pH 8. The pH of the PBS buffer is adjusted using an additive, such as Sodium Hydroxide. It will be understood that the pH may be adjusted to create alternative formulations consistent with this disclosure. For example, the pH of the compound may be adjusted such that the permselectivity of the resulting PoAP can be modified. More particularly, PoAp may be formulated to have a defined molecular weight cutoff. That is, by adjusting the pH of the formulation, the PoAP may be modified to substantially restrict the passage of molecules having a molecular weight larger than the cutoff molecular weight. Accordingly, the PoAP can be modified according to the molecular weight of the contaminants that need to be restricted from reaching the platinum wire. It will also be understood that other monomers may be selected, and these alternative monomers may provide the desired functional characteristics at a different pH. The 2-Aminophenol and PBS mixture is electropolymerized into Poly-Ortho-Aminophenol (PoAP.)

Optionally, the oxides or oxide layers may be removed from the surface of the conductive platinum substrate as illustrated in block 805. As described earlier, these oxides or layer of oxides dramatically restrict the surface area available to the hydrogen peroxide to react with the platinum. By removing these oxides or oxide layers, for example by chemical etching or physical buffing, a less contaminated platinum wire may be provided for coating. In this way, the surface area of platinum available for hydrogen peroxide interaction is dramatically increased, thereby increasing the overall electrical sensitivity of the sensor.

The interference compound is then applied to the conductive substrate as shown in block 807. In one particular application, the interference compound is electrodeposited onto the conductive substrate, which deposits the compound in a thin and uniform layer. Further, the electrodeposition process facilitates a chemical cross-linking of the polymers as the PoAP is deposited. It will be understood that other processes may be used to apply the polymer to the conductive substrate.

As described above, the interference membrane has a compound that is self-limiting in thickness. The overall allowable thickness for the membrane may be adjusted according to the ratio between the monomer and the buffer, as well as the particular electrical characteristics used for the electropolymerization process. Also, the interference membrane may be formulated for a particular permselective characteristic by adjusting the pH. It will also be understood that a cyclic voltammetry (CV) process may be used to electrodeposit the interference membrane compound, such as PoAP. A CV process is generally defined by having (1) a scanning window that has a lower voltage limit and upper voltage limit, (2) a starting point and direction within that scanning window, (3) an elapsed time for each cycle, and (4) the number of cycles completed. It will be understood by one skilled in the art that these four factors can provide nearly infinite alternatives in the precise application of the interference membrane compound. In one example, the following ranges have been found to be effective for the CV process to apply PoAP:

Scanning window: −1.0V to 2.0V
Starting point: −0.5V to 0.5 VV
Rate: x-y cycles per minute
Cycles 5-50

As illustrated in step 811, the enzyme layer is then applied, which includes the glucose oxidase, and then a glucose limiting layer is applied as shown in 818. This glucose limiting layer, as discussed above, is useful to limit the number of glucose molecules that are allowed to pass into the enzyme layer.

Finally, as illustrated in block 821, an insulator may be applied to the reference wire. In many cases, the reference wire will be a silver/silver oxide wire, and the insulator will be an ion limiting layer that is nonconductive of electrons.

Glucose-Limiting Layer

Figure 9A:
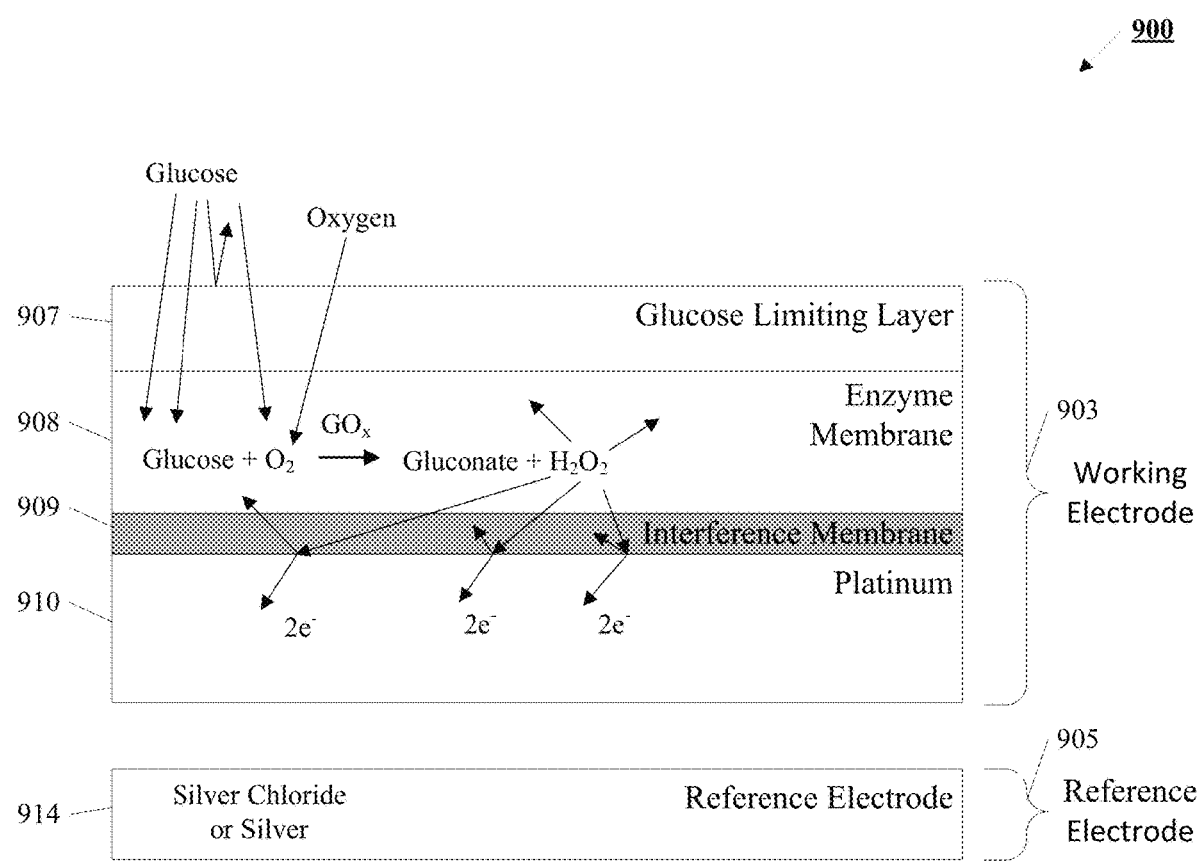
FIG. 9A is a not-to-scale cross-sectional block diagram of a 2-wire sensor having an interference membrane layer and a glucose limiting layer in accordance with some embodiments.

Referring now to FIG. 9A, a sensor 900 is illustrated for use with a continuous biological monitor. Sensor 900 has a working electrode 903 and a reference electrode 905. The silver/silver chloride reference electrode 914, the conductive layer 910, the interference membrane 909, and enzyme layer 908 are similar to those as discussed previously with reference to sensor 700, so will not be discussed in detail. It will be understood that several alternatives exist for these layers consistent with this disclosure.

Sensor 900 has a glucose limiting membrane layer 907. As will be described, the glucose limiting membrane 907 may be manufactured using simple and inexpensive manufacturing techniques, and provides a more uniform glucose limiting membrane with more precise regulation for the glucose molecules. In this way, the level of glucose molecules permitted to pass into the enzyme layer may be more precisely and uniformly defined and controlled, and resulting calculations and results are enabled to be more linear and precise. The glucose limiting membrane 907 is constructed to provide a thin conformal layer of a physically cross-linked material that is easy to dispose and that provides exceptional uniformity, glucose molecule control, and linearity results. In one specific example, the physically cross-linked material uses hydrogen-bonds. Importantly, the glucose limiting layer does not rely upon chemical cross-linking.

Although the present glucose limiting layer 907 is illustrated with sensor 900, it will be appreciated that the glucose limiting layer 907 may also be advantageously used on other sensors, such as prior art sensor 600. It will be appreciated that the present glucose limiting layer may be broadly used on other types of biological sensors.

As formulated in FIG. 9A, the glucose limiting layer 907 may be formulated to provide a uniform layer that more evenly and precisely passes glucose molecules into the enzyme layer 908 than typical prior art glucose limiting layers, which results in a more stable, consistent, and accurate generation of free electrons. As the sensor 900 more evenly and uniformly passes glucose and generates electrons, the sensor is more accurate, has less sensitivity to noise, is more stable, and is more readily calibrated.

Figure 9B:
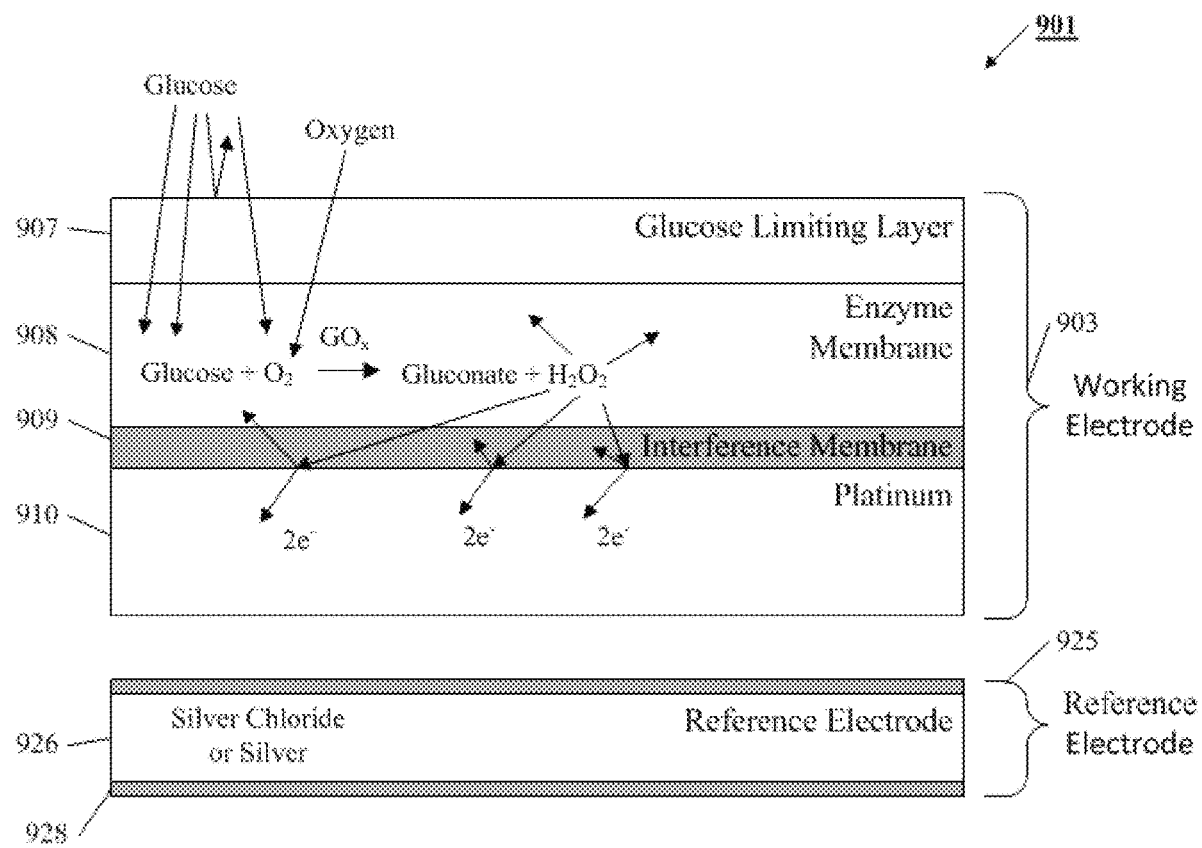
FIG. 9B is a not-to-scale cross-sectional block diagram of a 2-wire sensor having an interference membrane layer, a glucose limiting layer, and a coated reference electrode in accordance with some embodiments.

Referring now to FIG. 9B, another sensor 901 for a continuous biological monitor is illustrated. Sensor 901 is similar to sensor 900, so will not be described in detail. Sensor 901 has the same working electrode 903 as described with reference to sensor 900. However, sensor 901 has a reference wire 925 that has a silver/silver chloride layer 926 surrounded by an ion limiting membrane 928. The application of this ion limiting membrane 928 over the silver/silver chloride layer 926 desirably controls the current sensitivity of the overall sensor device 901 by controlling the flow of ions from the silver/silver chloride layer. In this way, current sensitivity may be advantageously controlled and defined.

Figure 10:
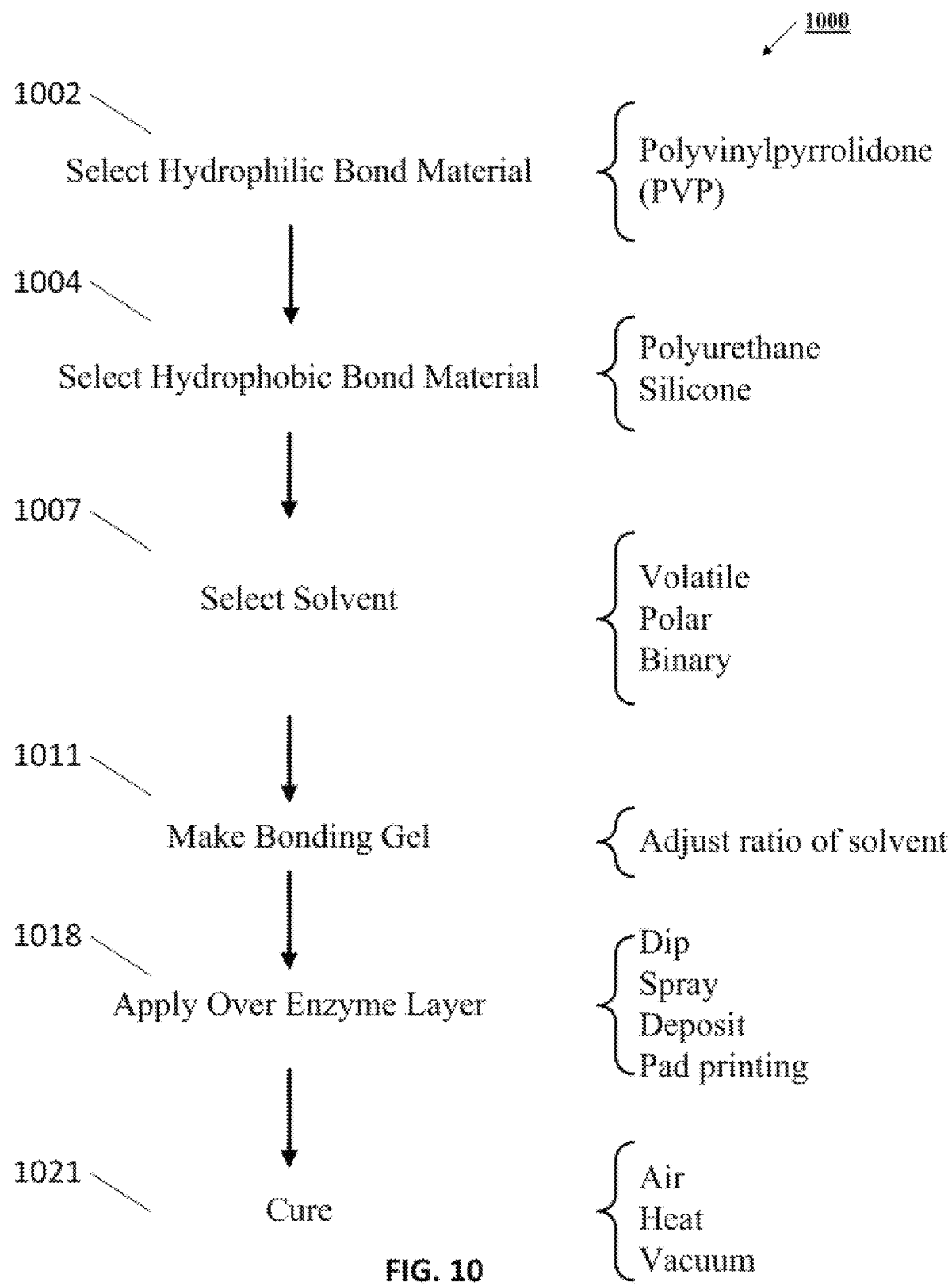
FIG. 10 is a flowchart of general manufacturing steps for making and applying a glucose limiting layer in accordance with some embodiments.

Referring now to FIG. 10, a process 1000 for creating a glucose limiting layer is generally described. Before providing details and examples, the process is generally described. First, a hydrophilic bonding material is selected as shown in step 1002. Also, a hydrophobic bonding material is selected as shown in step 1004, and a solvent is selected as illustrated in step 1007. The hydrophilic bonding material, the hydrophobic bonding material, and the solvent are mixed together in a desired ratio, which results in a bonding gel as illustrated in step 1011. This bonding gel may then be applied over the enzyme layer 1018 on the working wire. The gel then cures to form strong and resilient hydrogen-bonded structures as illustrated at 1021. It will be understood that other materials may be used, and that other types of physical crosslinking may be formed.

In selecting the hydrophilic bonding material 1002, it is desirable to identify a hydrophilic bonding material that has a relatively high molecular weight, for example 1 to 5 million. It has been found that hydrophilic bonding material with a molecular weight of 1 to 3 million is particularly effective. As understood, the molecular weight of a polymer is the sum of the atomic weights of all the atoms in the molecule. Accordingly, the selected hydrophilic bonding material is typically a significantly large polymer. Further, the hydrophilic body material is selected to be readily dispensable in standard manufacturing processes, and to have the ability to form strong hydrogen bonds. Although in some embodiments the hydrophilic bonding material has a relatively high molecular weight, is readily dispensable, and has strong hydrogen bonds capability, it will be understood that other characteristics may become important depending upon the specific application. For example, Polyvinyl alcohol, Polyacrylic acid, or Polyvinylpyrrolidone (PVP) may be used as a hydrophilic bonding material for the glucose limiting layer. In one specific example, PVP, in its pharma grade form, has a molecular weight of about 1.3 million. It will be understood that other polymers may be found with similar or other desirable characteristics.

The hydrophobic bond material is then selected 1004. In particular, the hydrophobic material is selected based on a desirable biocompatibility, as well as a ratio between hard and soft segments. Generally, hydrophobic materials are formed of segments of small monomers which are cross-linked to much larger polymer sections. A higher proportion of soft segments allows the hydrophobic bond material to have a higher degree of interaction with the solvent and hydrophilic bonding material; however, the higher ratio of soft segments also decreases the hydrophobic characteristic of the material, as the small segments tend to be hydrophilic. As to the hard segments, a higher ratio of hard segments provides for a stronger physical characteristic, which is often measured as a Shore hardness using a durometer. In this way, a hydrophobic material may be selected that has an appropriate level of interaction with the solvent and hydrophilic materials, as well as having sufficient hardness to act effectively as a protective coating. In some embodiments, polyurethane may be used as a hydrophobic bond material, with the desired characteristics of both providing sufficient hardness, as well as desirable interaction with the hydrophilic bond material (e.g., PVP) and the selected solvent. Additionally, silicones may also be used as the hydrophobic bonding material. It will also be appreciated that other types of hydrophobic bonding materials may be selected according to application-specific needs The third material in step 1007 is the solvent. Generally, a solvent is selected that is polar, binary, and sufficiently volatile for the curing needs. First, the solvent should have sufficiently strong polar characteristics to assist in properly aligning the hydrophilic and hydrophobic bonding materials. Second, as the solvent must dissolve both the hydrophilic and the hydrophobic material, the solvent should be selected for advantageous dissolving characteristics for each of the selected bonding materials. It will be understood that there are trinary solvents that can be substituted. Finally, the volatility of the solvent should be selected to support the desired cure characteristics. For example, some applications may need to be completed in a short period of time, thus requiring a fast flash solvent. In other cases, less volatile solvents may be substituted. In one example, a mixture of a heavy organic compound with an alcohol may provide a desirable solvent for the glucose limiting layer. In a specific example, the heavy organic compound may be tetrahydrofuran (THF) or Dimethylformamide (DMF), and the alcohol may be ethanol. It will be understood that other compounds may be used that can provide the desirable characteristics of the solvent.

The hydrophilic bonding material, hydrophobic bond material, and solvent are mixed together to form a bonding gel in step 1011. The viscosity of the bonding gel may be tuned by adjusting the ratio of the solvent to the bonding materials. The bonding gel can then be applied over the enzyme layer in step 1018. The bonding gel is easy to work with, and may be dipped, sprayed, deposited or pad printed using various manufacturing processes. The bonding gel is then cured in step 1021, which may be done in ambient air, by using added heat, or by using added vacuum. It will be understood that other processes may be used to either speed or slow the curing process. As the bonding material cures, the hydrophobic and hydrophilic physically cross-link, and in particular, form hydrogen bonds. The resulting hydrogen bonded layer enables a highly desirable uniform and even passage of glucose molecules as compared to prior chemically bonded layers.

Enzyme Layer

As discussed with reference to sensors 600, 700, and 900, the working wire for each sensor has a respective enzyme layer 608, 708 and 908. As is well known, the enzyme layer facilitates a chemical interaction between glucose and glucose oxidase (GOx), which generates hydrogen peroxide ($H_2O_2$). The hydrogen peroxide further reacts with a conductive platinum substrate, which generates a current of free electrons that can be measured, with the measured level of current being proportional to the level of glucose in the bloodstream or in another bodily fluid, such as ISF. To make a useful membrane for a glucose sensor, GOx is often stabilized with glutaraldehyde, imidoesters (dimethyl adipimidate, dimethyl suberimidate), hydroxysuccinimide and its derivatives. Typically, a formulation of about 0.6% glutaraldehyde is mixed with the GOx, and the mixture is then applied to the working wire. It will be understood that other ratios may be used, and that there may be other additives in the mixture. It is well known that polyaziridine may also be used as a stabilizer for GOx, but it suffers from similar disadvantages as glutaraldehyde.

Unfortunately, even with proper mixing, the GOx does not disperse evenly within the glutaraldehyde, leaving portions of the enzyme layer with a higher concentration of GOx and portions with a lower concentration of GOx. This uneven distribution of GOx causes a non-uniform interaction between glucose and GOx, which leads to an uneven generation of hydrogen peroxide. That is, given a constant level of glucose, different portions of the enzyme layer will generate more or fewer hydrogen peroxide molecules, resulting in more or fewer free electrons. In this way, the measured glucose level may vary based on where on the enzyme layer the glucose molecule lands and reacts. This uncertainty and variability due to uneven GOx dispersion may lead to an erroneous blood sugar reading.

Further, commercial GOx is derived from bacterial or fungal sources and as such is known to be cytotoxic, that is, harmful to cells. Even when GOx is stabilized with glutaraldehyde, some GOx may move within the layer and leech from the enzyme layer into the subject's body. Since none of the known protective layers for an enzyme layer can fully entrap GOx, there is a risk that at least some GOx may be exposed to the subject's cells.

Figure 11:
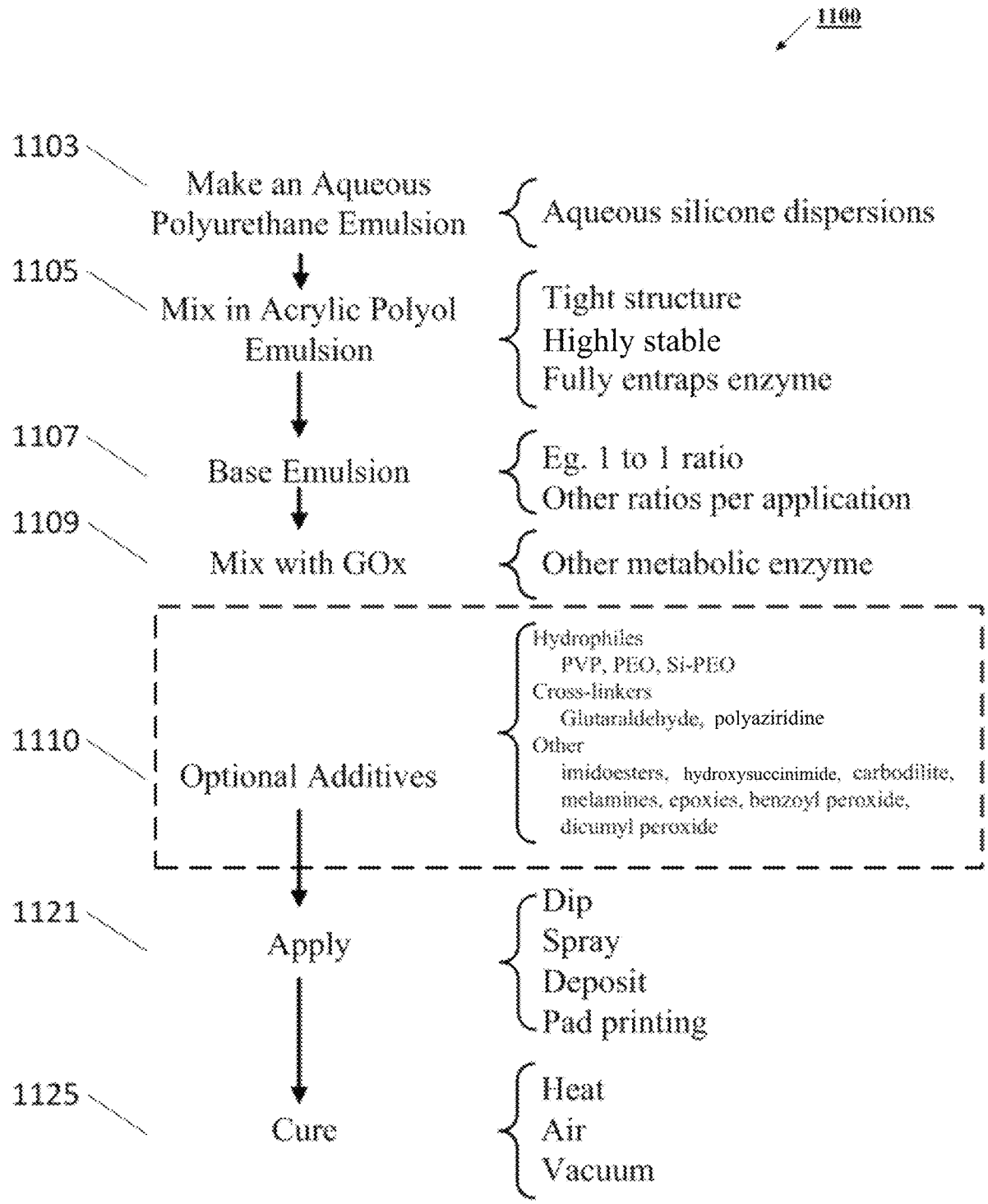
FIG. 11 is a flowchart of general manufacturing steps for making and applying an enzyme layer in accordance with some embodiments.

To address the deficiencies in the known glutaraldehyde-stabilized GOx, embodiments of an enzyme layer are provided that provide for substantially improved GOx entrapment and even distribution. As shown in FIG. 11, the enzyme layer is made using a process 1100. An aqueous emulsion of polyurethane is made as shown at step 1103. It will be understood that the amount of water that is mixed with the polyurethane may be adjusted according to application-specific requirements. Although polyurethane shall be used in the description of FIG. 11, it will be understood that other emulsions may be substituted, such as aqueous silicone dispersions. As illustrated at step 1105, the aqueous polyurethane emulsion is mixed with an aqueous acrylic polyol emulsion. The acrylic polyol acts as a self cross-linker with the polyurethane to generate a highly stable and tight structure that is able to fully entrap the GOx. The combination of the polyurethane emulsion from step 1103 and the acrylic polyol emulsion from step 1105 generates a base emulsion in step 1107. Depending upon application-specific requirements, the ratio of polyurethane to acrylic polyol may be adjusted; however, in one example approximately equal amounts of each are mixed together to form the base emulsion in step 1107. In some embodiments, GOx is blended with the polyurethane at a ratio of about 1 part GOx to 60 parts polyurethane by volume. It will be understood that other ratios may be used depending upon the particular application. It will also be understood that if other metabolic functions are to be tested other than glucose levels, other enzymes may be used.

As shown in block 1110 other optional additives may be added. For example, one or more hydrophiles may be added to the emulsion mixture to facilitate better mixing or to provide a more appropriate viscosity for application. Examples of hydrophiles that may be used in the formulation of the enzyme layer include PVP, PEO and Si-PEO. Si-PEO is understood to include silanes and PDMS PEO. It will be understood that other hydrophiles may be used. Although the acrylic polyol can provide for self cross-linking as it cures, other cross-linking polymers may be added for additional cross-linking. For GOx, such cross-linkers may include, for example, glutaraldehyde, imidoesters, hydroxysuccinimide, carbodilite, melamines, epoxies and polyaziridines.

The polyurethane/GOx blend is applied to the working electrode in step 1109, for example, by spraying, dipping, depositing or printing, 1121. The blend is cured in step 1125, at which time the layer cross-links to provide a stable dispersion of GOx.

Advantageously, the polyurethane/GOx blend, being an aqueous emulsion, is safe, easy to handle and apply, and provides for an even distribution of GOx. Further, as the cross-linked polymers are fully stabilized and entrapped within the layer, GOx is not able to move from the enzyme layer to the subject's body, eliminating safety concerns. Also, as the polyurethane/GOx blend is more stable than prior art enzyme layers, it has a longer usable shelf life, and exhibits the ability to support a higher loading. With a higher loading of GOx, the polyurethane/GOx blend has increased sensitivity and enables higher signal to noise ratios.

Sensors

Figure 12:
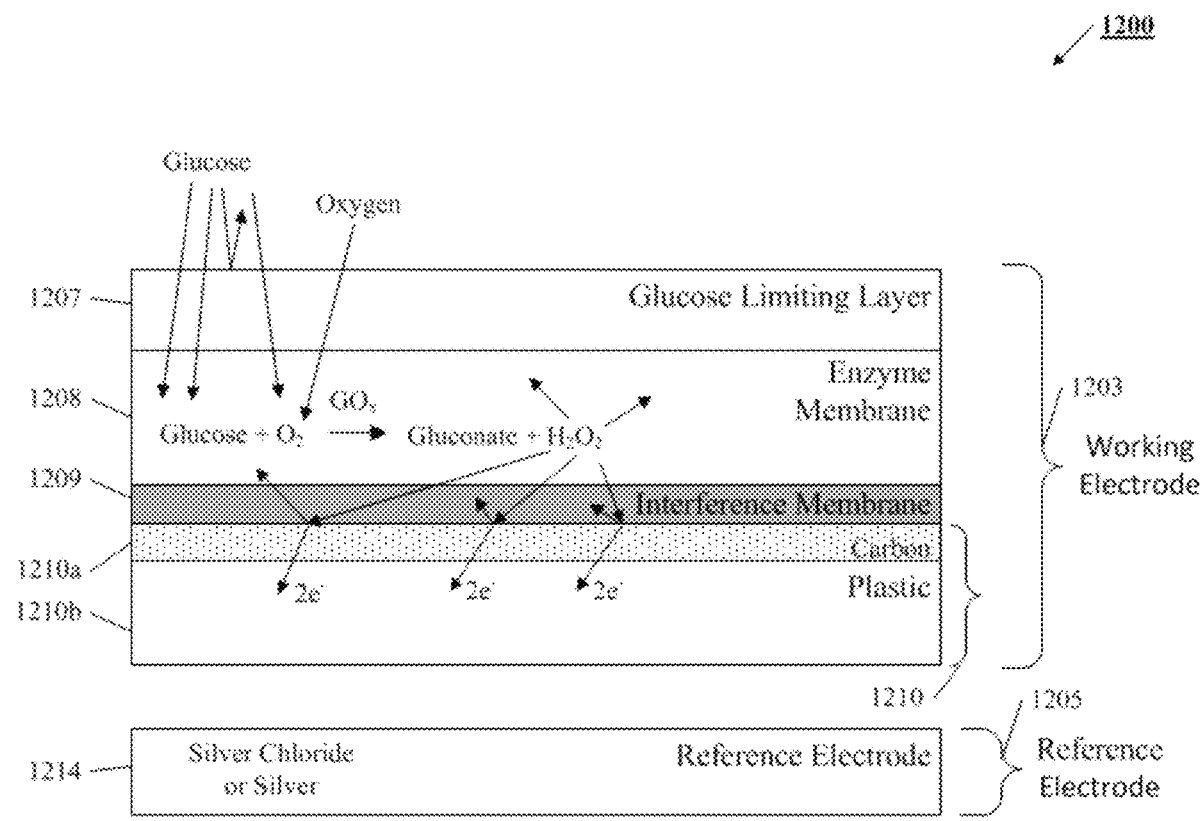
FIG. 12 is a not-to-scale cross-sectional block diagram of a 2-wire sensor having an enzyme layer, an interference layer, a glucose limiting layer, and a non-platinum substrate in accordance with some embodiments.

Referring now to FIG. 12, a sensor 1200 according to some embodiments is illustrated. Sensor 1200 is constructed with a working electrode 1203 and a reference electrode 1205. As described previously, reference electrode 1205 is typically silver chloride or silver 1214. Working electrode 1203 has a glucose limiting layer 1207 as described with reference to FIG. 9A, FIG. 9B and FIG. 10. Working electrode 1203 also has an enzyme layer 1208 in contact with the glucose limiting layer 1207 as described with reference to FIG. 11. The enzyme layer 1208 is also in contact with an interference membrane 1209 as described with reference to FIG. 7A, FIG. 7B and FIG. 8. The interference membrane 1209 is supported by substrate 1210, as fully described with reference to FIGS. 4A-C and FIG. 5. As illustrated, substrate 1210 has a plastic substrate portion 1210b that has a carbon coating 1210a, as described with reference to FIGS. 4A-C and FIG. 5. It will be understood, as illustrated, that the carbon coating 1210a will include a catalyst for hydrogen peroxide such as Phthalocyanine or Prussian blue.

Advantageously, as compared to prior sensors, sensor 700 provides an electrical signal with a higher signal-to-noise ratio, is less expensive to manufacture, and is safer for a patient to wear.

Enzyme Layer Having Direct Electron or Peroxide Generation

Figure 13A:
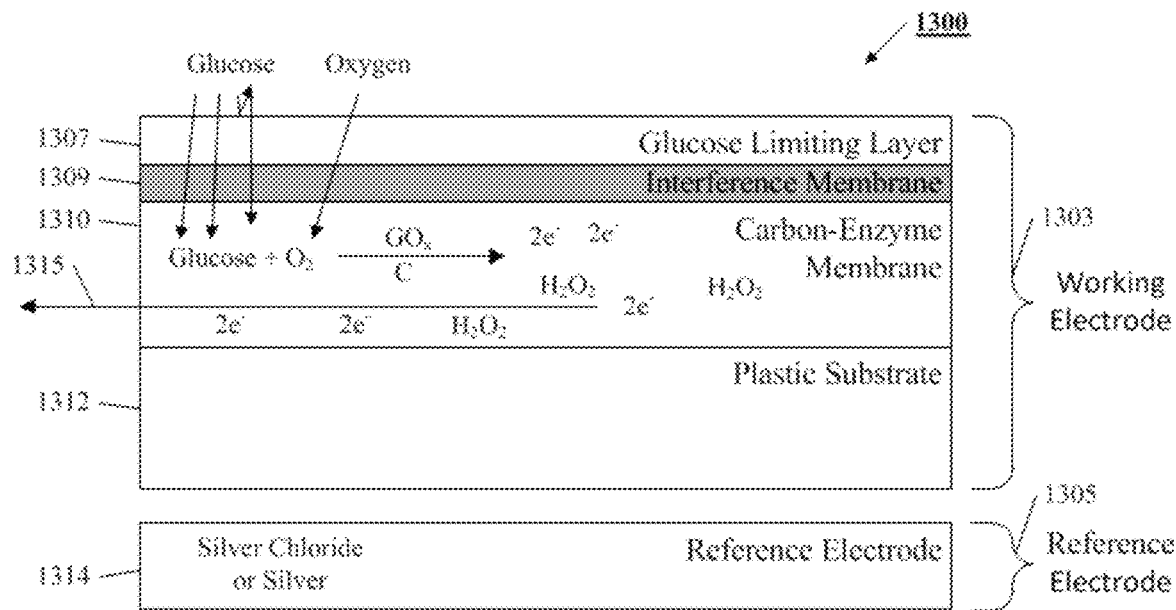
FIG. 13A is a not-to-scale cross-sectional block diagram of a 2-wire sensor having a carbon/GOx membrane for direct generation of electrons or peroxide and an interference layer in accordance with some embodiments.

Referring now to FIG. 13A, a sensor 1300 is illustrated. Sensor 1300 is illustrated as a two wire sensor having a working electrode 1303 and a reference electrode 1305. As described with previous sensors, the reference electrode 1305 is generally silver chloride or silver 1314. It will be understood that the construction of sensor 1300 may be any of the common structures for two wire sensors.

The working wire 1303 has a glucose limiting layer 1307. The glucose limiting layer may be of a known construction, but as illustrated, the glucose limiting layer 1307 is the glucose limiting layer described with reference to FIG. 9A and FIG. 9B. As described earlier, a glucose limiting layer is provided to limit and control the number of glucose molecules that may be passed from a patient's blood or ISF into the enzyme layer, thereby improving linearity of the overall sensor response. The glucose limiting layer still allows oxygen to travel to the enzyme layer. An interference membrane 1309 may be positioned below the glucose limiting layer 1307. In one example, the interference membrane 1309 is the interference membrane described with reference to FIG. 7A and FIG. 7B. As such, the interference layer 1309 is permselective to reject the passage of larger molecules. In this way, large molecules such as acetaminophen or other contaminants may be blocked from reaching the enzyme layer.

Sensor 1300 has a plastic material substrate 1312, such as a plastic wire. This plastic substrate material is selected to have sufficient strength for being inserted under the skin of a patient, as well as flexibility for patient comfort and ease of manufacturing. Further, it will be understood that the plastic substrate should be biologically safe and generally electrically unreactive. It will be understood that a wide range of materials meet the mechanical and functional requirements for the selected plastic substrate. For example, numerous organic polymers and thermoplastics may be used. For illustrative purposes only, the following specific plastic substrate materials may be used: polyethylene, polypropylene, polystyrene, polyvinyl chloride, and polylactic acid. It will be appreciated that a wide variety of materials may be used as the plastic substrate. This plastic substrate can be formed into an elongated wire in many shapes to support construction of different types of sensors. Generally, these plastic wires would be formed using well-known extrusion processes.

The plastic substrate 1312 supports a carbon-enzyme layer 1310. Generally, the new carbon-enzyme layer 1310 is prepared as a coating that is an aqueous dispersion of carbon materials, an elastomeric material, cross-linkers and GOx. For example, the carbon material may be in the form of graphite, graphene, diamagnetic graphite, pyrolytic carbon, carbon black, carbon paste, or carbon ink. In some cases, to support particular applications, other additives may be added to the carbon compound for enhanced electrical and response characteristics.

There are several acceptable elastomeric materials that would provide the desired characteristics, for example: polyurethane, silicone, acrylates or acrylics. It will be understood that other elastomeric materials may be substituted. Also, in some embodiments the carbon compound, after the elastomeric material is cured, does not delaminate from the plastic wire, in contrast to platinum coating of a Tantalum wire. In one example, an aqueous polyurethane emulsion is selected to be mixed with an aqueous acrylic polyol dispersion as a cross-linker. It will be understood that alternative or additional cross-linkers and other additives may be used.

As described with reference to sensor 1300, the GOx enzyme is used, as sensor 1300 is directed to detecting glucose levels. It will be understood that other enzymes such as lactate dehydrogenase (lactate), hydroxybutyrate dehydrogenase (ketone) may be used for other metabolic sensors. It will also be understood that if an enzyme other than GOx is used, additional modifications may be needed in the selection and ratios of materials in the carbon-enzyme layer.

The carbon-enzyme coating 1310 is applied to the plastic substrate 1312 and cured. As the aqueous dispersion cures on the plastic substrate, it crosslinks to a flexible but strong coating for the substrate, with the GOx evenly dispersed and fully entrapped. Further, the selected combination of the carbon materials provides for advantageous structural, mechanical, and electrical properties of the carbon-enzyme layer.

In operation, sensor 1300 permits glucose and oxygen to pass through the glucose limiting layer 1307 and the interference membrane 1309 into the carbon-enzyme layer 1310. The interference membrane 1309 blocks larger molecules that may contaminate or interfere with the chemical and electrical processes. Once the glucose and oxygen pass into the carbon-enzyme layer 1310, they react to form hydrogen peroxide, which then interacts with the carbon to generate free electrons. These free electrons may then be conducted as shown by arrow 1315 through the carbon-enzyme layer 1310 to the electronics of the sensor 1300.

Advantageously, sensor 1300 does not use any platinum, and has the GOx enzyme evenly dispersed and fully trapped within the carbon-enzyme layer. In this way, the sensor 1300 reduces the risk of potential safety issues with GOx, and provides a highly desirable level of sensitivity and high signal-to-noise performance.

Figure 13B:
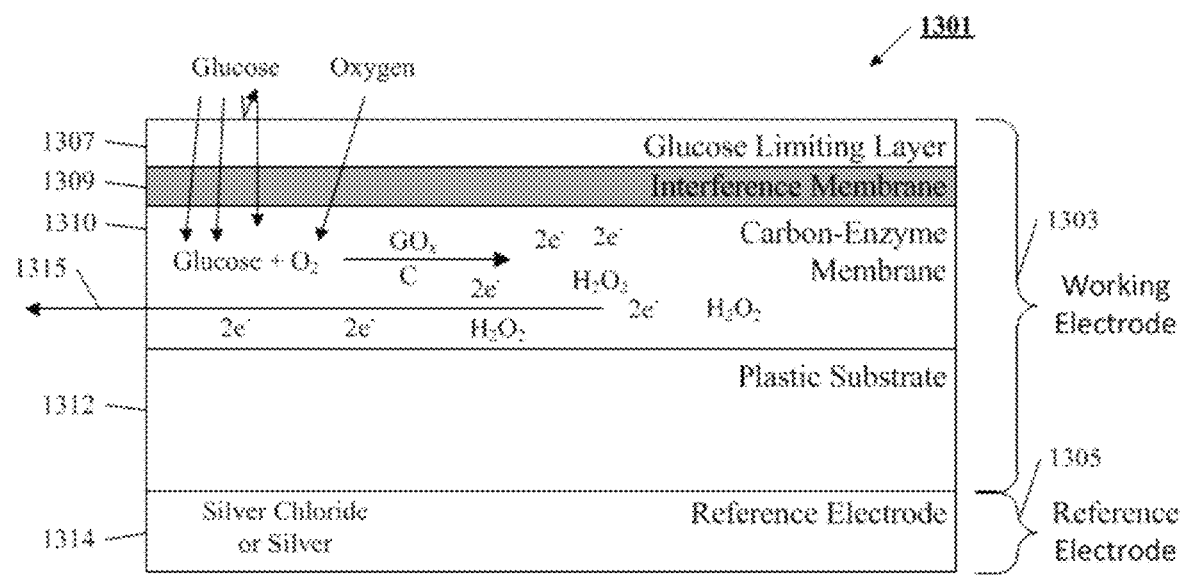
FIG. 13B is a not-to-scale cross-sectional block diagram of a 1-wire sensor having a carbon/GOx membrane for direct generation of electrons or peroxide and an interference layer in accordance with some embodiments.

Referring to FIG. 13B, sensor 1301 is illustrated. Sensor 1301 is similar to sensor 1300, so will not be described in detail. Sensor 1301 is a single wire sensor, where reference electrode 1305 is attached to working electrode 1303. It will be understood that such a physical construction may be achieved through various printing, extrusion and deposition processes.

Figure 14A:
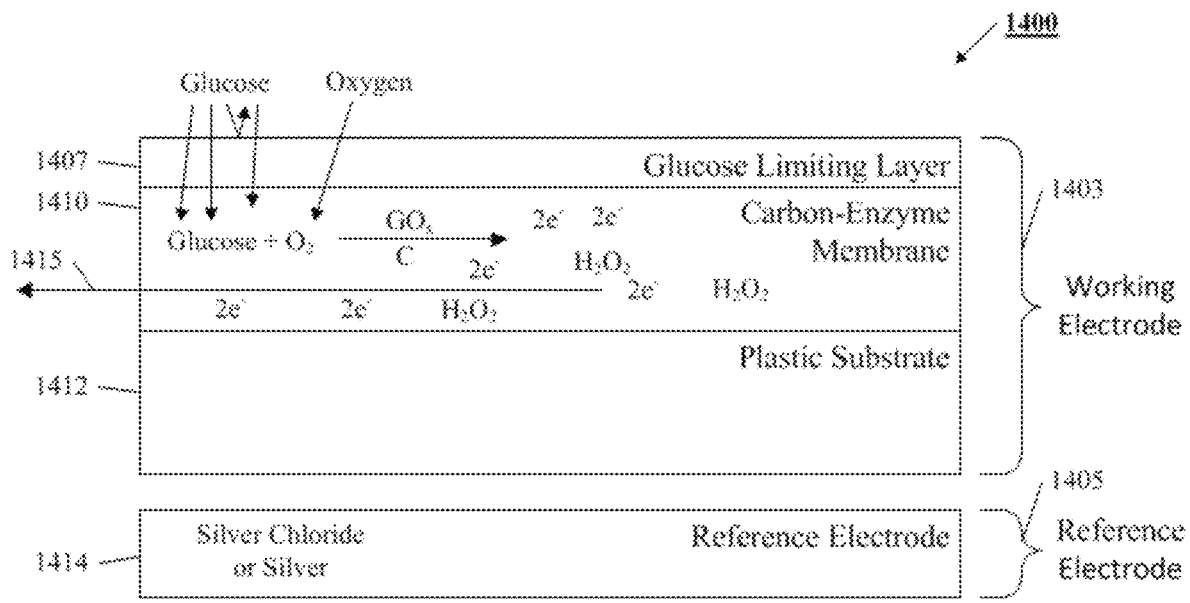
FIG. 14A is a not-to-scale cross-sectional block diagram of a 2-wire sensor having a carbon/GOx membrane for direct generation of electrons or peroxide in accordance with some embodiments.

Referring now to FIG. 14A, sensor 1400 is illustrated. Sensor 1400 is similar to sensor 1300, so will not be described in detail. As illustrated, sensor 1400 has a glucose limiting layer 1407 similar to glucose limiting layer 1307, a carbon-enzyme layer 1410 similar to carbon-enzyme layer 1310, plastic substrate 1412 similar to plastic substrate 1312, and reference electrode 1405 similar to reference electrode 1305, so none of these will be described in detail. As illustrated, sensor 1400 does not have an interference membrane. In some cases, an interference membrane will not be needed, as one of the primary purposes for the interference membrane is to protect large molecule contaminants from reaching and contaminating the platinum wire. Since sensor 1300 uses no platinum wire, the need for an interference membrane may be reduced.

Figure 14B:
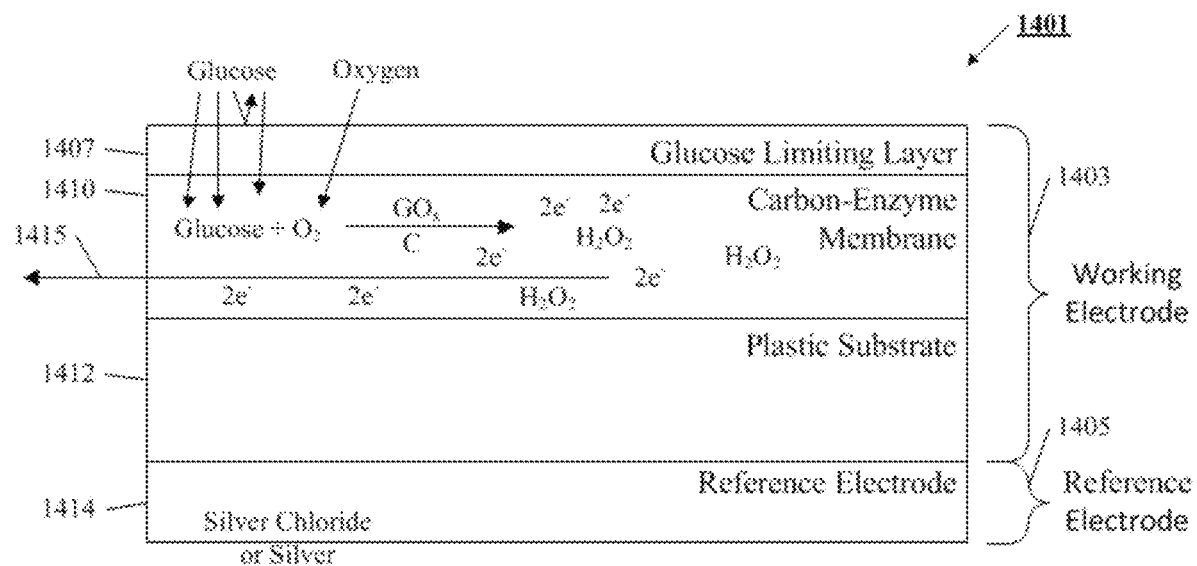
FIG. 14B is a not-to-scale cross-sectional block diagram of a 1-wire sensor having a carbon/GOx membrane for direct generation of electrons or peroxide and in accordance with some embodiments.

Referring to FIG. 14B, sensor 1401 is illustrated. Sensor 1401 is similar to sensor 1400, so will not be described in detail. Sensor 1401 is a single wire sensor, where reference electrode 1405 with silver chloride or silver 1414 is attached to working electrode 1403. It will be understood that such a physical construction may be achieved through various printing and deposition processes.

Figure 15:
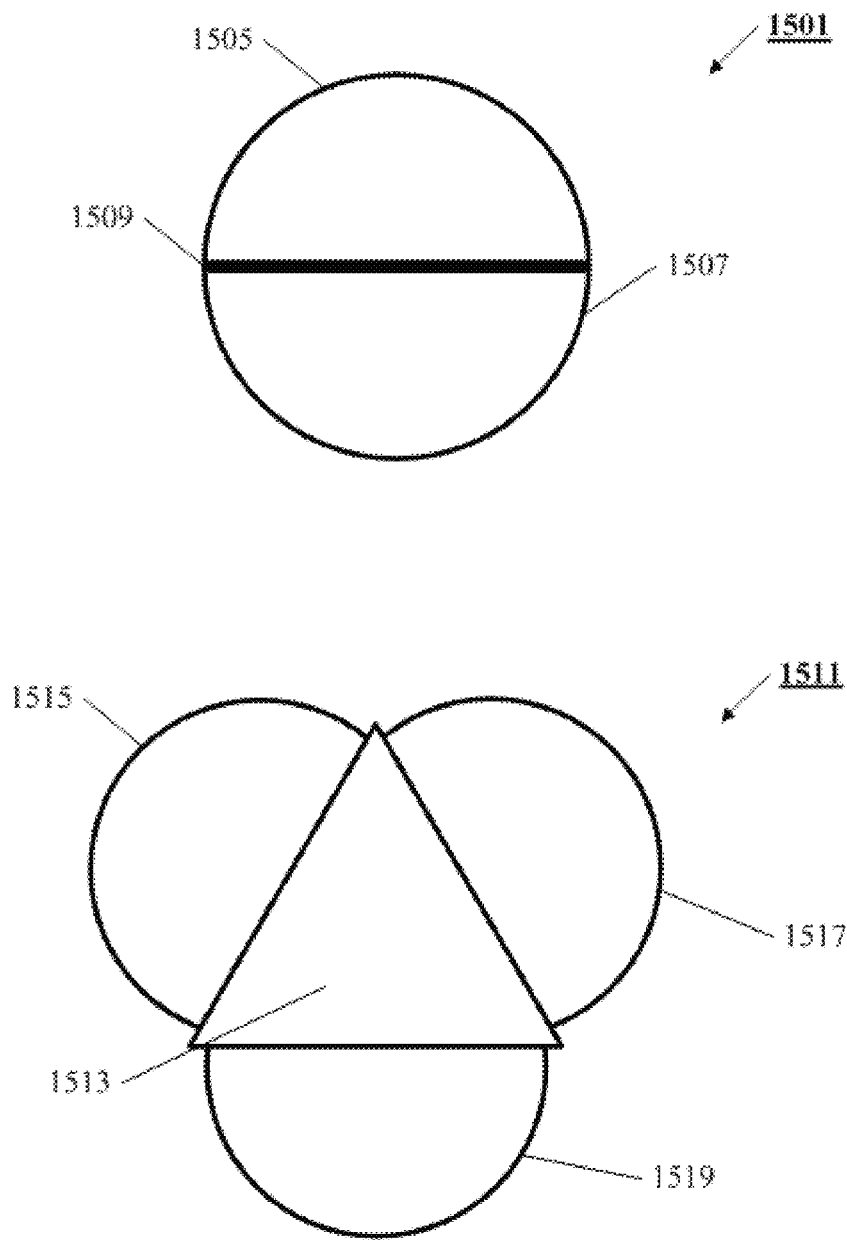
FIG. 15 is a not-to-scale cross-sectional block diagram of 1-wire sensors having a working wire with a carbon/GOx membrane for direct generation of electrons or peroxide and an attached reference wire in accordance with some embodiments.

Referring now to FIG. 15, single wire sensor 1501 is illustrated. Sensor 1501 has a working wire 1505 that is physically attached to a reference wire 1507, where both working wire 1505 and reference wire 1507 have semicircular cross-sections with flat surfaces facing each other. In some cases, an insulating member 1509 may be positioned at the flat surface interface between the working wire 1505 and the reference wire 1507. In some embodiments, the working wire 1505 may be the working wire described with reference FIG. 13B or FIG. 14B. Still referring to FIG. 15, another single wire sensor 1511 is illustrated. Single wire sensor 1511 has a reference wire 1515 attached to an insulated substrate 1513 that has a triangular cross-section. In one example, the substrate 1513 may be an extruded plastic wire. Also attached to the substrate 1513 is a reference electrode 1517 and a counter electrode 1519. In some embodiments, the working wire 1515 may be the working wire described with reference FIG. 13B or FIG. 14B. The reference wire 1515, reference electrode 1517 and counter electrode 1519 have flat surfaces that face the substrate 1513.

Figure 16:
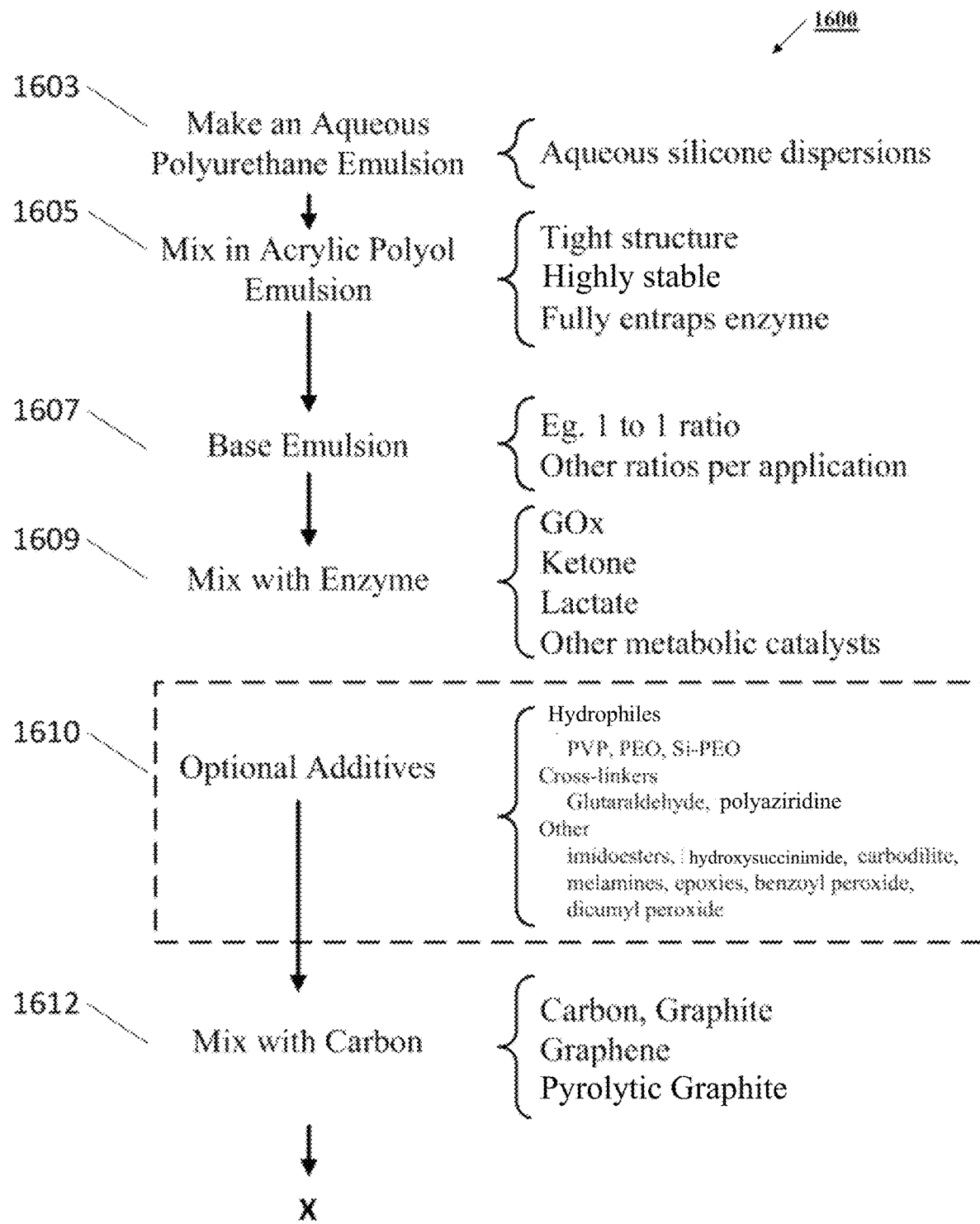
FIG. 16 is a flowchart of general manufacturing steps for making and applying a carbon/GOx membrane for direct generation of electrons or peroxide in accordance with some embodiments.
Figure 16:
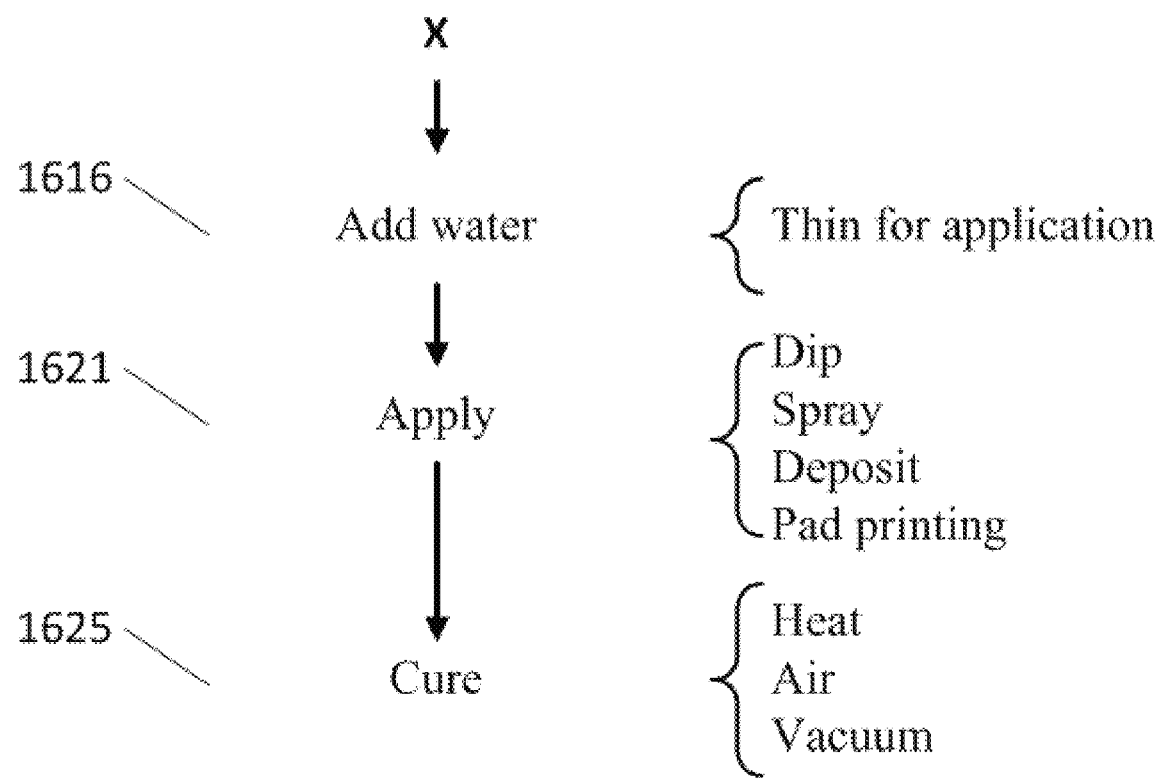

Referring now to FIG. 16, a process 1600 for making and applying the carbon-enzyme layer as shown in FIG. 13A, FIG. 13B, FIG. 14A and FIG. 14B is described. As discussed with reference to sensors 600, 700, and 900, the working wire for each sensor has a respective enzyme layer 608, 708 and 908. As is well known, the enzyme layer facilitates a chemical interaction between glucose and glucose oxidase (GOx), which generates hydrogen peroxide ($H_2O_2$). The hydrogen peroxide further reacts with a conductive platinum substrate, which generates a current of free electrons that can be measured, with the measured level of current being proportional to the level of glucose in the bloodstream or ISF. To make a useful membrane for a glucose sensor, GOx is often stabilized with glutaraldehyde. Typically, a formulation of about 0.6% glutaraldehyde is mixed with the GOx, and the mixture is then applied to the working wire. It will be understood that other ratios may be used, and that there may be other additives in the mixture. It is well known that polyaziridine, imidoesters, hydroxysuccinimide, carbodilite, melamines, epoxies, benzoyl peroxide, dicumyl peroxide may also be used as a stabilizer for GOx, but it suffers from similar disadvantages as glutaraldehyde.

Unfortunately, even with proper mixing, the GOx does not disperse evenly within the glutaraldehyde, leaving portions of the enzyme layer with a higher concentration of GOx and portions with a lower concentration of GOx. This uneven distribution of GOx causes a non-uniform interaction between glucose and GOx, which leads to an uneven generation of hydrogen peroxide. That is, given a constant level of glucose, different portions of the enzyme layer will generate more or fewer hydrogen peroxide molecules, resulting in more or fewer free electrons. In this way, the measured glucose level may vary based on where on the enzyme layer the glucose molecule lands and reacts. This uncertainty and variability due to uneven GOx dispersion may lead to an erroneous blood sugar reading.

Further, GOx is known to be cytotoxic, that is, harmful to cells. Even when GOx is stabilized with glutaraldehyde, some GOx may move within the layer and leech from the enzyme layer into the subject's body. Since none of the known protective layers for an enzyme layer can fully entrap GOx, there is a risk that at least some GOx may be exposed to the subject's cells.

Additionally, most known sensors use substrate of either solid platinum or a platinum coated metal wire. Either way, platinum is expensive, and leads to a higher priced sensor. The platinum is also susceptible to oxidation, which can lead to instability and a low signal-to-noise ratio. As discussed with reference to FIG. 4A, FIG. 4B, FIG. 4C and FIG. 5, a carbon compound may be applied over a plastic substrate, removing the need for any platinum in the working wire. As was described with reference to process 500, the carbon coating can be constructed to be flexible, strong, with desirable electrical characteristics, and applied in a manner that it will not delaminate from the plastic substrate.

To address the deficiencies in the known glutaraldehyde-stabilized GOx, and the expense of platinum, a new carbon-enzyme layer is provided that provides for substantially improved GOx entrapment and even distribution, with carbon in the same layer to provide strength, flexibility, and appropriate electrical characteristics. Further, the carbon-enzyme layer has been found to provide for a direct generation of free electrons, not only eliminating the need for any ion conducting layer or platinum wire, but providing for enhanced stability and substantially improved signal-to-noise ratios.

As shown in FIG. 16, the carbon-enzyme layer is made using a process 1600. An aqueous emulsion of polyurethane is made as shown at step 1603. It will be understood that the amount of water that is mixed with the polyurethane may be adjusted according to application-specific requirements. Although polyurethane has proven to perform well, it will be understood that other emulsions may be substituted, such as aqueous silicone dispersions As illustrated at step 1605, the aqueous polyurethane emulsion is mixed with an aqueous acrylic polyol emulsion. The acrylic polyol acts as a self cross-linker with the polyurethane to generate a highly stable and tight structure that is able to fully entrap the GOx. The combination of the polyurethane emulsion in step 1603 and the acrylic polyol emulsion in step 1605 generates a base emulsion in step 1607. Depending upon application-specific requirements, the ratio of polyurethane to acrylic polyol may be adjusted; however, in one example approximately equal amounts of each are mixed together to form the base emulsion in step 1607. In one embodiment, GOx is blended with the polyurethane at a ratio of about 1 part GOx to 60 parts polyurethane by volume. It will be understood that other ratios may be used depending upon the particular application. It will also be understood that if other metabolic functions are to be tested other than glucose levels, other enzymes may be used such as ketone, lactate, or other metabolic catalysts in step 1609.

As shown in block 1610 other optional additives may be added. For example, one or more hydrophiles may be added to emulsion mixture to facilitate better mixing or to provide a more appropriate viscosity for application. Well known hydrophiles include PVP, PEO and Si-PEO. Si-PEO is understood to include silanes and PDMS PEO. It will be understood that other hydrophiles may be used. Although the acrylic polyol can provide for self cross-linking as it cures, other cross-linking polymers may be added for additional cross-linking. For GOx, such cross-linkers may include, for example glutaraldehyde and polyaziridine.

A blend of carbon material is also mixed into the emulsion in step 1612. The carbon materials and ratios are selected according to application and functional requirements. For example, carbon (graphite) may be added to increase strength of the resulting layer, while graphene, pyrolytic graphite or a blend of graphene and pyrolytic graphite may be added to provide for improved electrical characteristics. The ratio of graphite to be added will be selected to provide sufficient strength for the resulting carbon-enzyme layer, but still permit sufficient flexibility in the layer so as not to delaminate from the plastic substrate or be so brittle as to crack. Also, the amount of graphene and pyrolytic graphite can be adjusted to set a desirable resistance for the carbon-enzyme layer. It will be understood that other forms of carbon may be substituted.

As the final mixture is prepared in step 1612, additional water or one or more hydrophiles (such as PVP) may be added in step 1616 to obtain the proper viscosity and fluid properties (e.g., to thin the mixture) to facilitate both even dispersion of the GOx, and to enable the selected application technique.

While a particular order for adding components of the polyurethane/GOx/C blend in step 1612 has been illustrated, it will be understood that the order may be changed without affecting the resulting layer. The polyurethane/GOx/C blend is applied to the working electrode, for example, by spraying, dipping, depositing or printing in step 1621. The blend is cured in step 1625, at which time the layer cross-links to provide a stable dispersion of GOx.

Advantageously, the polyurethane/GOx/C blend, being an aqueous emulsion, is safe, easy to handle and apply, and provides for an even distribution of GOx. Further, as the cross-linked polymers are fully stabilized and entrapped within the layer, GOx is not able to move from the enzyme layer to the subject's body, reducing safety concerns. Also, as the polyurethane/GOx/C blend is more stable than prior enzyme layers, it has a longer usable shelf life, and exhibits the ability to support a higher loading. With a higher loading of GOx, the polyurethane/GOx/C blend has increased sensitivity and enables higher signal to noise ratios than known devices.

In one example of the applied carbon-enzyme emulsion in step 1621, the carbon-enzyme emulsion comprises the following:

0.5 to 2 parts polyurethane emulsion;
0.5 to 2 parts acrylic polyol emulsion;
0.5 to 2 parts carbon, comprising:
    0.5 to 1 parts graphite;
    0.0 to 1 parts graphene; and
    0.0 to 2 parts pyrolytic graphite;
0.0 to 3 parts water and hydrophile; and
0.01 to 0.1 parts GOx.

Although process 1600 has been discussed with reference to the GOx enzyme, it will be appreciated that other enzymes may be substituted according to the particular metabolic function to be monitored. For example, the following enzymes may be used in process 1600. It will be appreciated that other enzymes and metabolic functions can be used, for example:

| Enzyme | Metabolic Function |
|---|---|
| Lactate dehydrogenase | Lactate |
| Hydroxybutyrate dehydrogenase | Ketone |

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A working electrode for a subcutaneous sensor for use with a continuous biological monitor for a patient, comprising:
   a conductive substrate; and
   a carbon-enzyme layer on the conductive substrate, the carbon-enzyme layer comprising:
      a polyurethane crosslinked with an acrylic polyol;
      an enzyme fully entrapped by the polyurethane crosslinked with the acrylic polyol, the enzyme selected according to a biological function to be monitored; and
      a carbon material;
   wherein the carbon-enzyme layer is electrically conductive and facilitates a generation of either peroxide or electrons within the carbon-enzyme layer responsive to reacting the enzyme with a target biologic from blood of the patient.

2. The working electrode according to claim 1, further including a glucose limiting layer over the carbon-enzyme layer that limits an amount of glucose from the blood of the patient that passes to the carbon-enzyme layer.

3. The working electrode according to claim 1, wherein the enzyme is glucose oxidase (GOx), lactate dehydrogenase, lactate oxidase, or hydroxybutyrate dehydrogenase.

4. The working electrode according to claim 1, wherein the enzyme is glucose oxidase (GOx) and the biological function is glucose level.

5. The working electrode according to claim 1, wherein the polyurethane crosslinked with the acrylic polyol further comprises:
   an additional cross-linker selected from imidoesters, hydroxysuccinimides, carbodilites, melamines, epoxies, benzoyl peroxides or dicumyl peroxides.

6. The working electrode according to claim 1, wherein the carbon material comprises carbon, graphite, graphene, or pyrolytic graphite.

7. The working electrode according to claim 1, further comprising a hydrophile selected from polyvinylpyrrolidone (PVP), polyethylene oxide (PEO) or silane-PEO (Si-PEO).

8. The working electrode according to claim 1, wherein the carbon-enzyme layer has an approximate ratio of materials comprising:
   0.5 to 2.0 parts of the polyurethane;
   0.5 to 2.0 parts of the acrylic polyol;
   0.01 to 0.1 parts of the enzyme; and
   0.5 to 2.0 parts of the carbon material.

9. The working electrode according to claim 8, wherein the carbon material further comprises:
   0.5 to 1.0 parts of a graphite;
   0.0 to 1.0 parts of a graphene; and
   0.0 to 2.0 parts of a pyrolytic graphite.

10. The working electrode according to claim 8, wherein the carbon-enzyme layer further comprises 0.0 to 3.0 parts of water and a hydrophile.

11. A working electrode for a subcutaneous sensor for use with a continuous biological monitor for a patient, comprising:
    a conductive substrate; and
    a carbon-enzyme layer on the conductive substrate, the carbon-enzyme layer comprising:
       a silicone crosslinked with an acrylic polyol;
       an enzyme fully entrapped by the silicone crosslinked with the acrylic polyol, the enzyme selected according to a biological function to be monitored; and
       a carbon material;
    wherein the carbon-enzyme layer is electrically conductive and facilitates a generation of either peroxide or electrons within the carbon-enzyme layer responsive to reacting the enzyme with a target biologic from blood of the patient.

12. The working electrode according to claim 11, further including a glucose limiting layer over the carbon-enzyme layer that limits an amount of glucose from the blood of the patient that passes to the carbon-enzyme layer.

13. The working electrode according to claim 11, wherein the enzyme is glucose oxidase (GOx), lactate dehydrogenase, lactate oxidase, or hydroxybutyrate dehydrogenase.

14. The working electrode according to claim 11, wherein the enzyme is glucose oxidase (GOx) and the biological function is glucose level.

15. The working electrode according to claim 11, wherein the silicone crosslinked with the acrylic polyol further comprises:
    an additional cross-linker selected from imidoesters, hydroxysuccinimides, carbodilites, melamines, epoxies, benzoyl peroxides or dicumyl peroxides.

16. The working electrode according to claim 11, wherein the carbon material comprises carbon, graphite, graphene, or pyrolytic graphite.

17. The working electrode according to claim 11, further comprising a hydrophile selected from polyvinylpyrrolidone (PVP), polyethylene oxide (PEO) or silane-PEO (Si-PEO).

18. The working electrode according to claim 11, wherein the carbon-enzyme layer has an approximate ratio of materials comprising:
    0.5 to 2.0 parts of the silicone;
    0.5 to 2.0 parts of the acrylic polyol;
    0.01 to 0.1 parts of the enzyme; and
    0.5 to 2.0 parts of the carbon material.

19. The working electrode according to claim 18, wherein the carbon material further comprises:
    0.5 to 1.0 parts of a graphite;
    0.0 to 1.0 parts of a graphene; and
    0.0 to 2.0 parts of a pyrolytic graphite.

20. The working electrode according to claim 18, wherein the carbon-enzyme layer further comprises 0.0 to 3.0 parts of water and a hydrophile.

* * * * *